United States Patent [19]

Lombardino et al.

[11] 4,246,263

[45] Jan. 20, 1981

[54] ANTIINFLAMMATORY AND IMMUNOREGULATORY PYRIMIDINES, THEIR METHOD OF USE AND PHARMACEUTICAL COMPOSITIONS

[75] Inventors: Joseph G. Lombardino; Charles A. Harbert, both of Groton, Conn.

[73] Assignee: Pfizer Inc., New York, N.Y.

[21] Appl. No.: 85,011

[22] Filed: Oct. 15, 1979

[51] Int. Cl.³ ............ C07D 239/26; A61K 31/505
[52] U.S. Cl. .................... 424/251; 544/335; 544/242; 424/263; 546/339; 546/340; 546/341; 546/342; 546/344; 546/346
[58] Field of Search .............. 544/335; 424/251

[56] References Cited

U.S. PATENT DOCUMENTS 3,818,009  6/1974  Taylor et al. ................ 544/335

OTHER PUBLICATIONS

Chemical Abstracts vol. 49, Cols. 336–337, (1955) Abstracting Vejdelek et al. in "Chem. Listy," vol. 47, pp. 49–58 (1953).

*Primary Examiner*—Henry R. Jiles
*Assistant Examiner*—Robert T. Bond
*Attorney, Agent, or Firm*—Connolly and Hutz

[57] ABSTRACT

A series of 4-(2-hydroxyethylthiomethyl)pyridines and related compounds, and their pharmaceutically acceptable acid addition salts, having antiinflammatory and immunoregulatory activity are disclosed. Preferred compounds include 4-(2-hydroxyethylthiomethyl)pyridine itself, as well as 4-(2-hydroxyphenylthiomethyl)pyridine, 4-(2-hydroxy-1-propylthiomethyl)pyridine, 4-(3-hydroxy-2-butylthiomethyl)pyridine, 4-(2-hydroxyethylthiomethyl)pyrimidine, the acetate esters corresponding to the above compounds, and 4-(2,3-dihydroxy-1-propylthiomethyl)pyridine.

15 Claims, No Drawings

ANTIINFLAMMATORY AND IMMUNOREGULATORY PYRIMIDINES, THEIR METHOD OF USE AND PHARMACEUTICAL COMPOSITIONS

BACKGROUND OF THE INVENTION

This invention relates to pyridines and pyrimidines substituted at the 4-position with a thioether and hydroxy containing sidechain, the corresponding methyl ether and carboxylic acid ester derivatives thereof, and the acid addition salts of said alcohols, methyl ethers and esters.

A number of compounds have been known in the art to be useful as antiinflammatory agents, for example the corticosteroids, phenylbutazone, indomethacin, piroxicam and other benzothiazine dioxides (Lombardino, U.S. Pat. No. 3,591,584), 2-oxo-2,3-dihydrobenzofuran-3-carboxamides (Kadin, U.S. Pat. No. 3,676,463), and substituted diarylimidazoles (Lombardino, U.S. Pat. No. 3,707,475). Accordingly these compounds have therapeutic value in the treatment of arthritic and other inflammatory conditions. Such conditions have also been treated by administration of immunoregulatory agents, such as levamisole, as described, for example, in Arthritis and Rheumatism, 20, 1445 (1977) and Lancet, 1, 393 (1976). In efforts to find new and improved therapeutic agents for the treatment of these conditions, it has now been found that the novel pyridines and pyrimidines of the present invention are active either as antiinflammatory agents or as regulants of the immune response in mammals, and in many cases, possess both types of activity. Because these activities are complementary, the latter are of particular value in the treatment of rheumatoid arthritis and other conditions where relief of the inflammation and regulation of the immune response is desired.

The compounds of the present invention are novel. Isomeric 3-(2-hydroxyethylthiomethyl)pyridine has been reported in the literature [Vejdelek et al., Chem. Listy. 47, 49 (1953); see Chem. Abstr. 49, 336f (1955)]; no pharmacological activity, however, is reported for this compound.

SUMMARY OF THE INVENTION

In accordance with the present invention, it has been unexpectedly found that certain novel pyridine and pyrimidine derivatives, together with their pharmaceutically acceptable acid addition salts, are useful when used therapeutically as either antiinflammatory agents or as regulators of the immune response. They are particularly useful in conditions such as rheumatoid arthritis where both antiinflammatory and immunoregulatory agents have been used individually for therapeutic purposes.

The structures of the novel therapeutic agents of this invention are

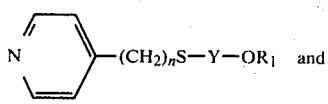 and

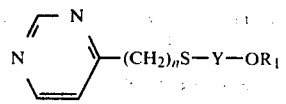

and the pharmaceutically acceptable acid addition salts thereof, wherein n is an integer, 1 or 2;

Y is a carbon radical as follows:
ethylene (—CH$_2$—CH$_2$—), propylene (—CH$_2$—CH$_2$—CH$_2$—), ethylene substituted with up to two methyl groups and up to one phenyl group

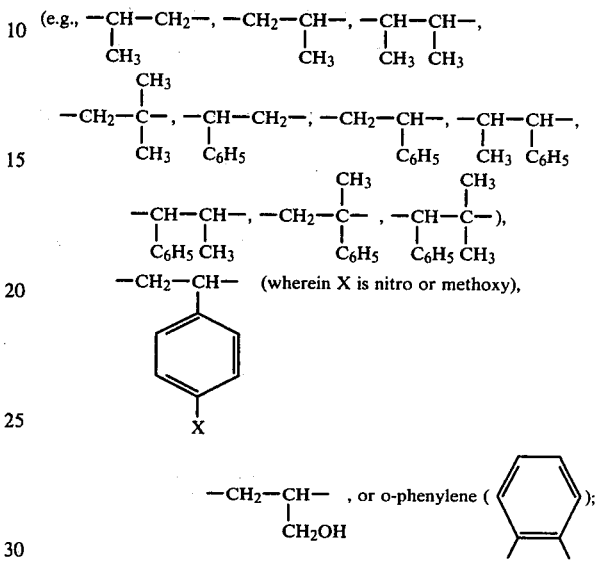

and R$_1$ is selected from the group consisting of hydrogen, methyl, benzoyl or alkanoyl of 2 to 5 carbon atoms

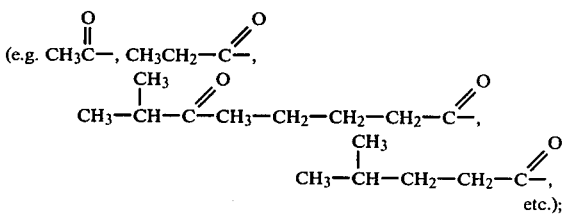

with the proviso that when Y is

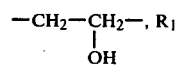

is hydrogen.

Preferred among these compounds are the pyridines in which Y is o-phenylene, ethylene,

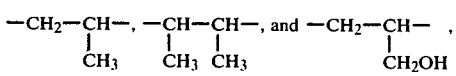

particularly in the form of the alcohol or acetate ester (i.e. R$_1$ is hydrogen or acetyl). Because of its excellent oral activity both as an antiinflammatory agent and as an immunoregulatory agent, the most highly preferred compound (which can also be formed in vivo as a metabolite of the acetate ester) is 4-(2-hydroxyethylthiomethyl)pyridine itself.

Antiinflammatory activity is reflected in the so-called rat foot edema test, in which the ability of an oral dose of the compound to inhibit an inflammatory reaction is measured, while immunoregulatory activity is assessed by the so-called mouse E-rosette procedure in which the ability of the test compound to restore erythrocyte rosette formation in thymectomized mice is measured. These tests are described in greater detail below.

This invention also encompasses pharmaceutical compositions of the above enumerated pyridine and pyrimidine derivatives, as well as their use as antiinflammatory and immunoregulatory agents in therapy.

DETAILED DESCRIPTION OF THE INVENTION

A variety of convenient methods are available for the preparation of the pyridine-alcohols, ethers and esters of the present invention. The methods are enumerated as follows:

(1) Reaction of 4-picolyl mercaptan or 2-(4-pyridyl)ethyl mercaptan with a suitably substituted halohydrin. For example:

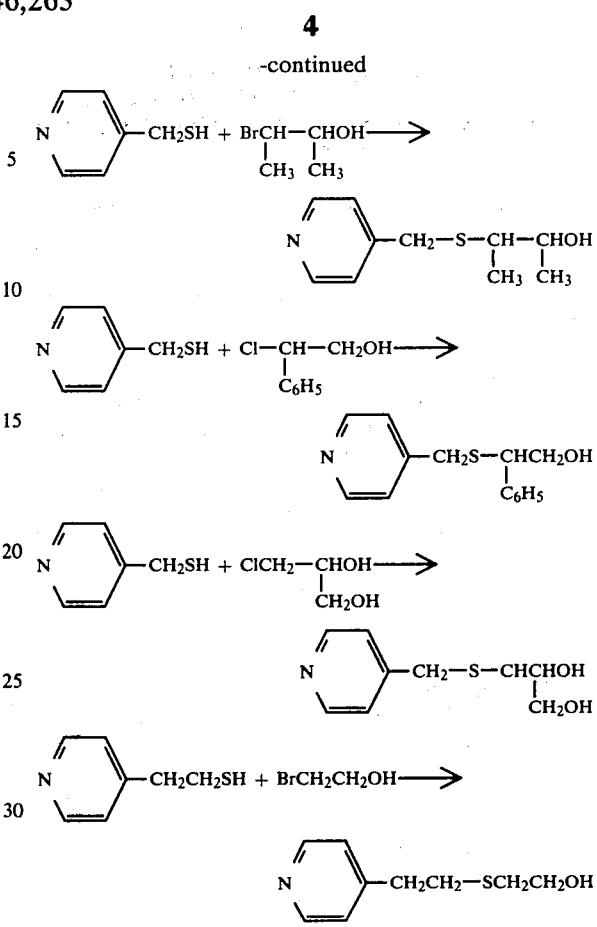

(2) Reaction of 4-picolylmercaptan or 2-(4-pyridyl)ethyl mercaptan with an alpha-haloacid or ester, followed by suitable hydride reduction to the alcohol, or addition of a suitable Grignard reagent. For example:

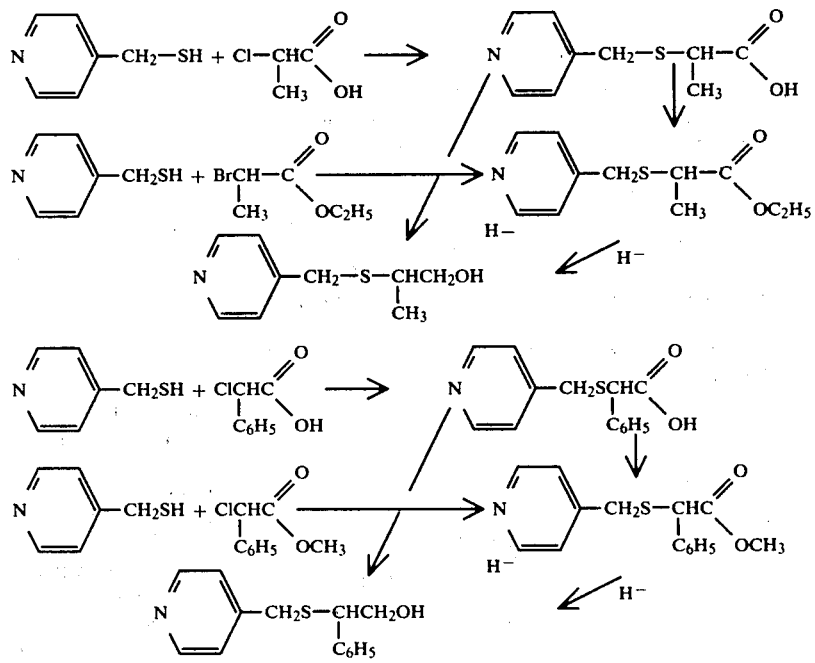

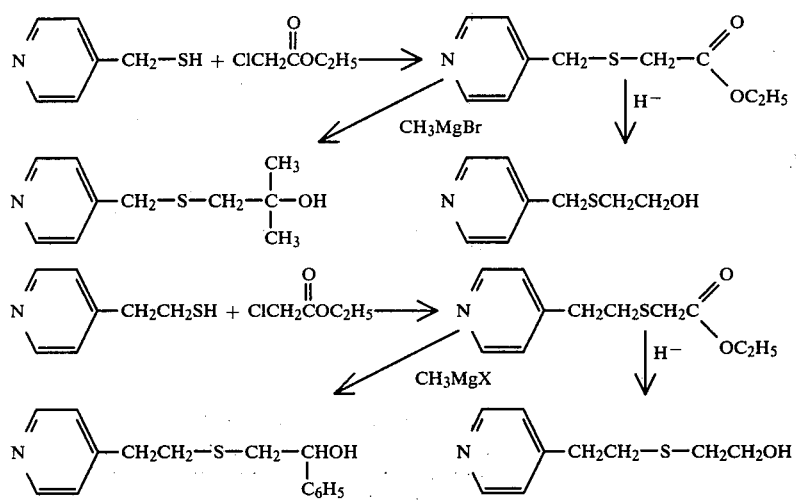

(3) Reaction of 4-picolyl mercaptan or 2-(4-pyridyl)ethyl mercaptan with an alpha-haloketone or alpha-haloaldehyde (preferably protected as the acetal), followed by deprotection if necessary and then either suitable hydride reduction or addition of an appropriate Grignard reagent. For example:

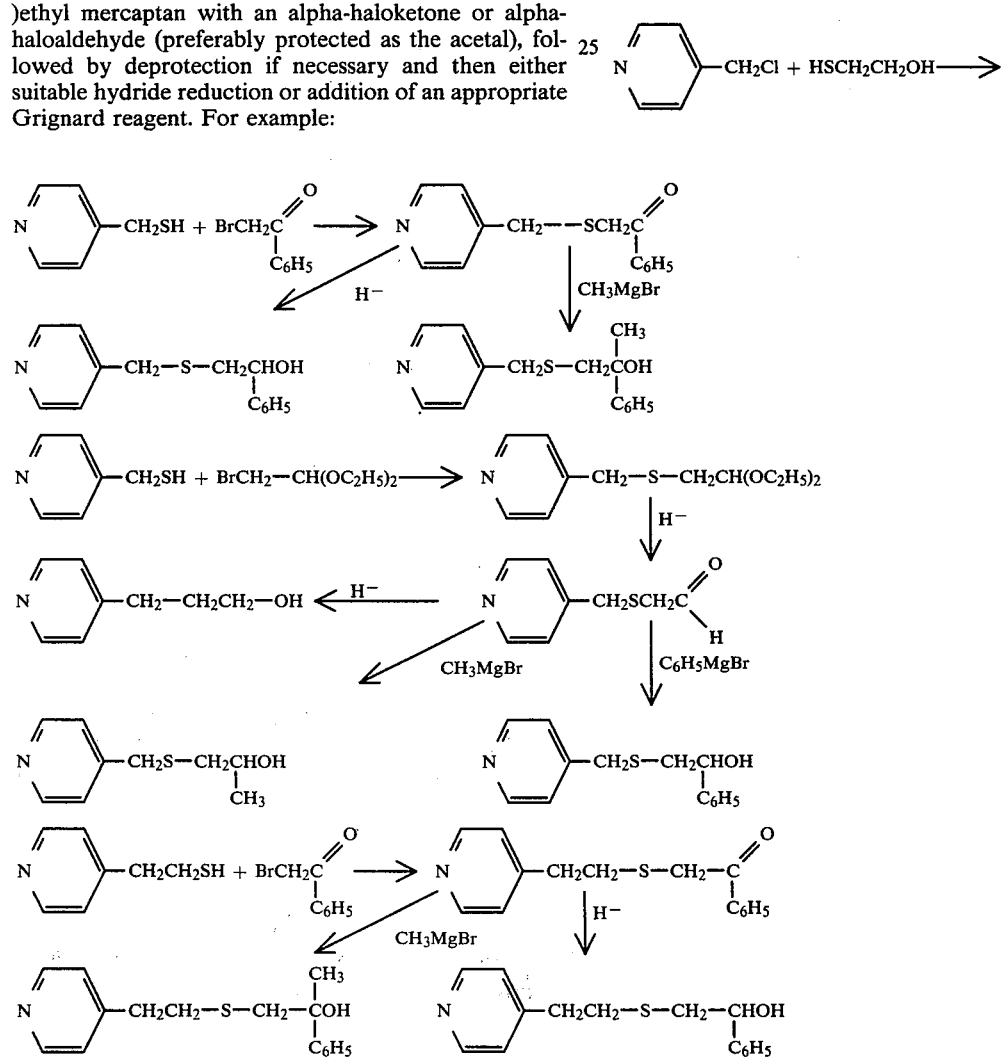

(4) The reaction of 4-picolyl halide or 2-(4-pyridyl)ethyl halide with a suitable substituted mercaptan (cf. method 1 above). For example:

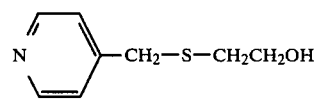

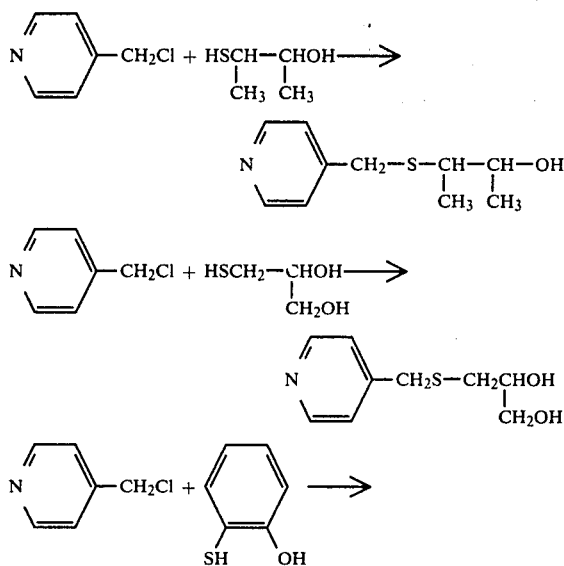

(5) The reaction of 4-picolyl halide or 2-(4-pyridyl)ethyl halide with an alpha-mercapto acid or alpha-mercapto ester, followed by suitable hydride reduction or addition of a suitable Grignard reagent (cf. method 2 above). For example:

(6) The reduction of 4-picolyl halide or 2-(4-pyridyl)ethyl halide with an alpha-mercapto ketone, followed by hydride reduction or reaction with an appropriate Grignard reagent (cf. Method 3). For example:

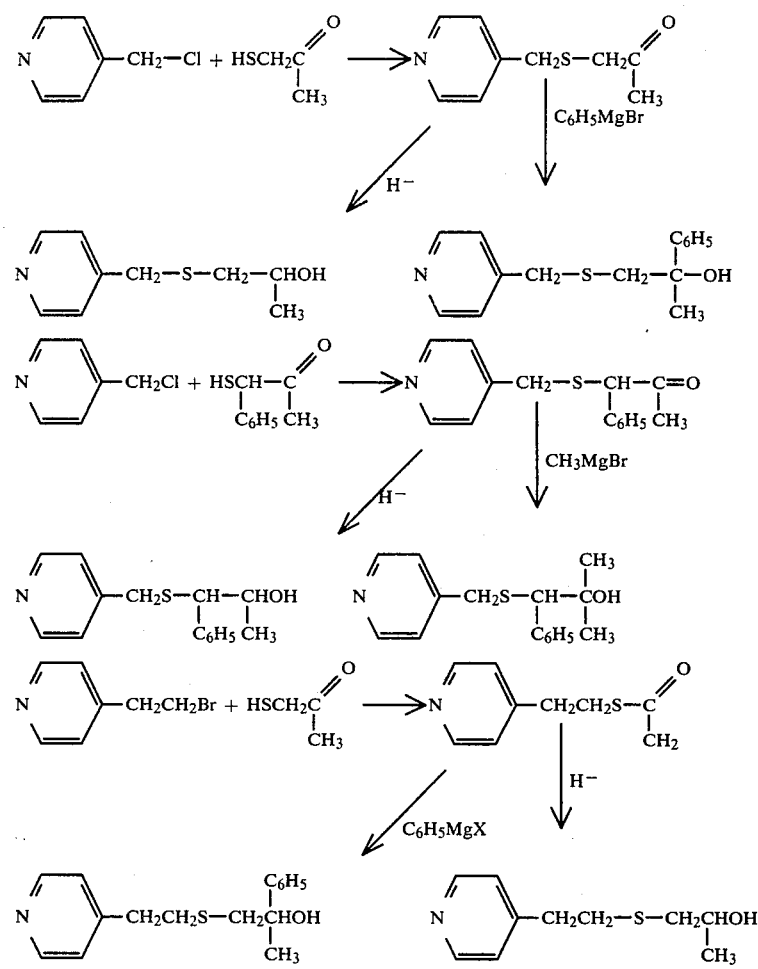
(7) Addition of mercaptoalcohols, mercaptoesters or mercaptoketones to 4-vinylpyridine, followed by hydride reduction or addition of a Grignard reagent as appropriate. For example:
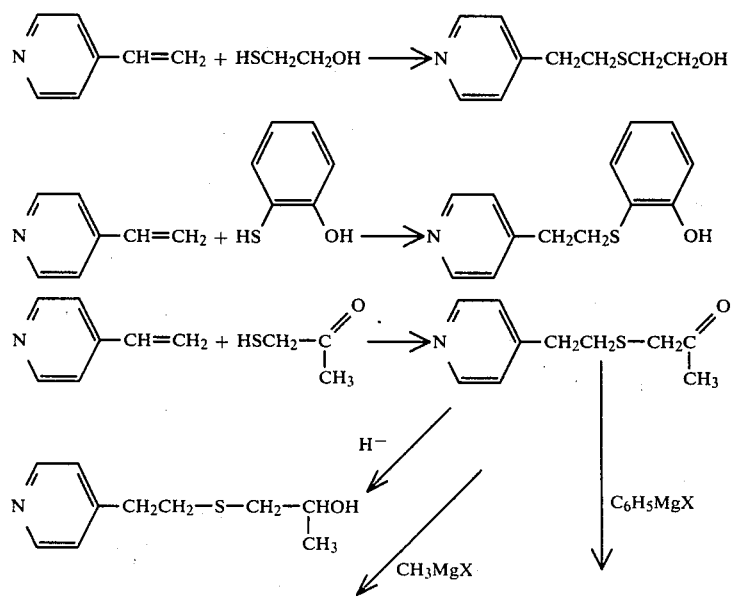

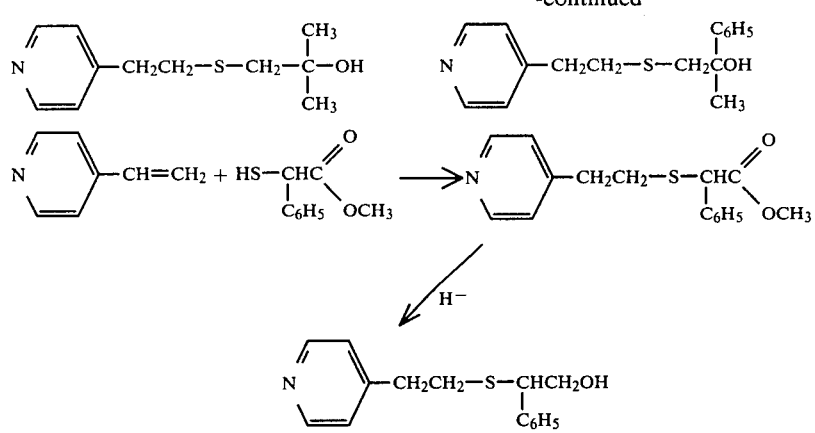

(8) Acylation or alkylation of the alcohols prepared by methods (1) to (7).

Preparation methods (1) to (6) in all cases involve a reaction in which the halogen of an organic halide is replaced by an organic thio residue. The reaction is facilitated by using an equivalent of strong base to convert the mercaptan to anionic salt, which is much more efficient in converting the organic halogen to the thio ether. When an acid salt of the pyridine moiety (e.g. 4-picolyl chloride hydrochloride) or an acid (e.g. alpha-mercaptopropionic acid) is employed as one of the reactants, a compensating amount of base is added. A wide variety of solvents are suitable for this reaction, including alcohols, acetonitrile, dimethylformamide, etc., the only requirement being that the solvent be inert towards reactants and product, and that the reactants have some degree of solubility. Preferably, the solvent should be less acidic than the mercaptan, so as to facilitate formation of the thio anion. The temperature employed for this reaction is not critical (e.g. 0°–120° C.). It should be high enough to provide a reasonable rate, but not so high as to lead to undue decomposition. As is well known in the art, rate will vary with the nature of the organic halide (rate: I>Br>Cl), the structure of both the halide and the mercaptan, and the solvent. The reaction time should be such that the reaction is nearly complete (e.g. >95% conversion when equivalent amounts of halide and mercaptan are employed) to maximize yields (e.g. 1 hour to several days). These reactions are readily monitored by thin layer chromatography, employing one of a variety of commercially available silica gel plates containing an ultraviolet indicator. Suitable eluants are chloroform/methanol mixtures with the proportion of these solvents varied with the polarity of the reaction product, a practice well-known in the art. For most of the reactions of this type, an eluant consisting of 9 parts of chloroform and 1 part of methanol is well suited. For the more polar compounds the proportion of methanol is increased (e.g. 4 chloroform/1 methanol). It is sometimes advantageous to add up to 5% acetic acid to the eluant, particularly when dealing with acid addition salts. Ethyl acetate and other alcohols (e.g. butanol) as well as a proportion of water can also be employed in the eluant. As the reaction proceeds, an equivalent of strong acid is produced, neutralizing the mole of base used in the reaction. For this reason pH can also be used as an aid in monitoring this reaction.

The method (7), addition of mercaptans to 4-vinylpyridine is carried out under conditions of temperature and solvent which correspond to those for the replacement of organic halogen by organic thio radical as discussed above. In this case also, suitable reaction times can be determined by use of the same thin layer chromatography systems.

The hydride reductions required in methods (2), (3), (5), (6) and (7) above can be carried out with a variety of reagents, generally under mild conditions. The most common commercially available metal hydride reducing agents are, in order of decreasing activity, lithium aluminum hydride, lithium borohydride, and sodium borohydride. The latter can be activated by addition of lithium chloride or aluminum chloride. Also commercially available is a less reactive derivative of lithium aluminum hydride sold under the tradename "Red-al", which is a 70% solution of bis(2-methoxyethoxy)aluminum hydride in benzene, and lithium aluminum hydride as a 50% suspension in oil, which is more readily handled than lithium aluminum hydride itself. The reduction of carboxylic acids and esters (methods 2 and 5) requires a strong hydride reducing agent such as lithium aluminum hydride itself or sodium borohydride activated with aluminum chloride. It is essential that the solvent for such a hydride reduction be aprotic and free of reducible groups (carbonyl function of any type, nitrile, nitro, aliphatic halogen, sulfonate etc.). The preferred solvents are ethers such as tetrahydrofuran, dioxane, 1,2-dimethoxyethane, bis(2-methoxyethyl)ether, etc. Temperature and reaction time are not critical, usually being in the range 0°–100° C. for up to 24 hours. For reduction of esters (methods 2, 5 and 7) the same reagents as those employed for reduction of acids can be employed. Lithium borohydride alone can also be employed, but more vigorous conditions (e.g. refluxing tetrahydrofuran) are required. Also well-suited for the reduction of esters is Red-al (discussed above). Suitable solvents for use with Red-al are toluene, benzene, diethylether, tetrahydrofuran, dimethoxyethane, etc. Temperature and reaction times are as discussed immediately above. For reduction of aldehydes or ketones (methods 3, 6 and 7) but excepting aromatic nitro substituted ketone, the conditions employed for the reduction of acids and esters can also be used. Lithium borohydride, under mild conditions (e.g. 25° C. in tetrahydrofuran) with the same solvent considerations as discussed above for lithium aluminum hydride, can also be employed for reduction of ketones and aldehydes. Preferred, however, is the milder reagent, sodium borohydride. The latter reagent is generally employed in a non-acidic, protic solvent (water, $C_1$–$C_5$-alcohols) at temperatures of 85° C. or less (usually less than 35° C. in water). Reaction time is not critical, usually being in the range 1–24 hours. Sodium borohydride can also be employed in ether solvents, but the presence of a protic solvent is generally required for a reasonable rate of reduction to be attained. An even milder hydride reducing agent, sodium cyanoborohydride, is preferred for the reduction of ketone in the presence of an aromatic nitro functionality. Somewhat acidic water, or methanol is preferred with this reagent, although the pH is kept above 3 to avoid undue decomposition of the reagent. Temperature is usually in the range 0°–40° C., with reaction time up to 24 hours.

The Grignard reagent additions (methods 2, 3, 5, 6 and 7) are generally carried out by adding a solution of preformed Grignard reagent in ether solution to a solution of the free base form of the pyridine ester or ketone in an ether solvent such as tetrahydrofuran, dioxane or 1,2-dimethoxyethane at temperatures generally in the range 0°–60° C., conveniently at 0°–25° C., with reaction times up to 3 days.

The methyl ether derivatives of method (8) can be formed from the alcohols of methods (1) to (7) by use of methyl halides (preferably methyl iodide because of its excellent reactivity) or dimethyl sulfate, reacted with the preformed alkaline earth salt of the precursor alcohol in an inert, aprotic solvent such as a hydrocarbon (e.g. toluene, methylcyclohexane), an ether (e.g. tetrahydrofuran, dimethoxyethane), or other inert solvent (e.g. dimethylformamide). Reaction temperature, which is generally in the range 0°–100° C. is not critical, room temperature being acceptable. The reaction can be monitored by thin layer chromatography, as well as by pH, as described above for the reaction of organic halides with mercaptans.

A variety of means are available for the acylations of method (8). Most direct is the reaction of the free base form of the pyridine-alcohol (as prepared by methods 1–7) with an acid chloride or an acid anhydride. Additional base (inorganic or tertiary amine) can be added, if desired. Alternatively, an acid salt of the pyridine-alcohol can be acylated with the same reagents in the presence of an equivalent or more of added base. In a related procedure, the acid is reacted with a chloroformate, in the presence of an equivalent of a tertiary amine such as triethylamine, N-methylmorpholine, dimethylaniline, N-methylpiperidine, etc. to form a mixed anhydride which is then reacted with the pyridine alcohol. Solvents for these acylation reactions can be the anhydride itself, or any solvent which is aprotic and inert towards reactants and products, for example, halogenated hydrocarbons (e.g. methylene chloride), dimethylformamide, dimethylacetamide, ethers (e.g. tetrahydrofuran, 1,2-dimethoxyethane), etc.

The starting materials required for methods (1)–(7) are quite generally available from the literature or commercially. Aliphatic mercaptans can be prepared from the corresponding halides by reaction of the halide with thiourea to form the isothiuronium salt followed by basic hydrolysis (see Preparations 1 and 2 below), by reaction of organic halides with hydrogen sulfide or alkali metal hydrosulfide [e.g. mercaptoacetone, Hromatka et al., Monatsh. 78, 32 (1948)], or by hydrolysis of thiol esters [e.g. 2-methoxyethylmercaptan, 2-mercapto-1-propanol, alpha-mercapto-alpha-phenylacetone (Chapman et al., J. Chem. Soc., 579 (1950); Sjoberg, Ber. 75, 13 (1942); von Wacek et al., Ber 75, 1353 (1942)], while the only aromatic mercaptan required as a starting material for this invention, 2-mercaptophenol, is available commercially. Organic halides required as starting materials are also generally available commercially or in the literature. Typical methods for making the required halides are direct halogenation, action of hydrogen or phosphorous halides on an alcohol, or addition of hydrogen halides to epoxides. The requisite reagents, including hydride reducing agents and Grignard reagents, are available commercially.

The same convenient methods are available for the preparation of the pyrimidine alcohols, ethers and esters of the present invention. For example:

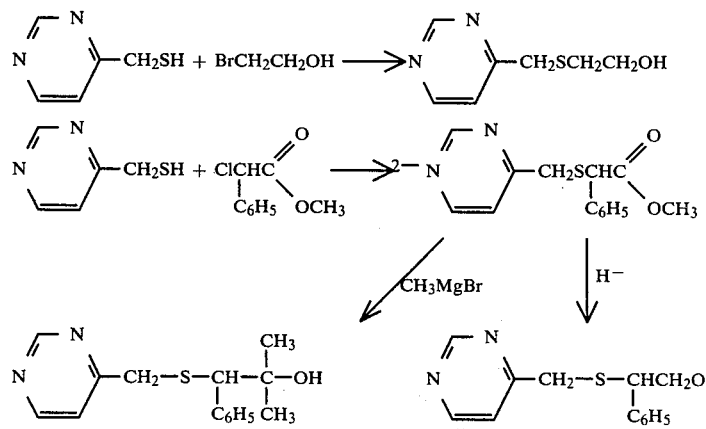

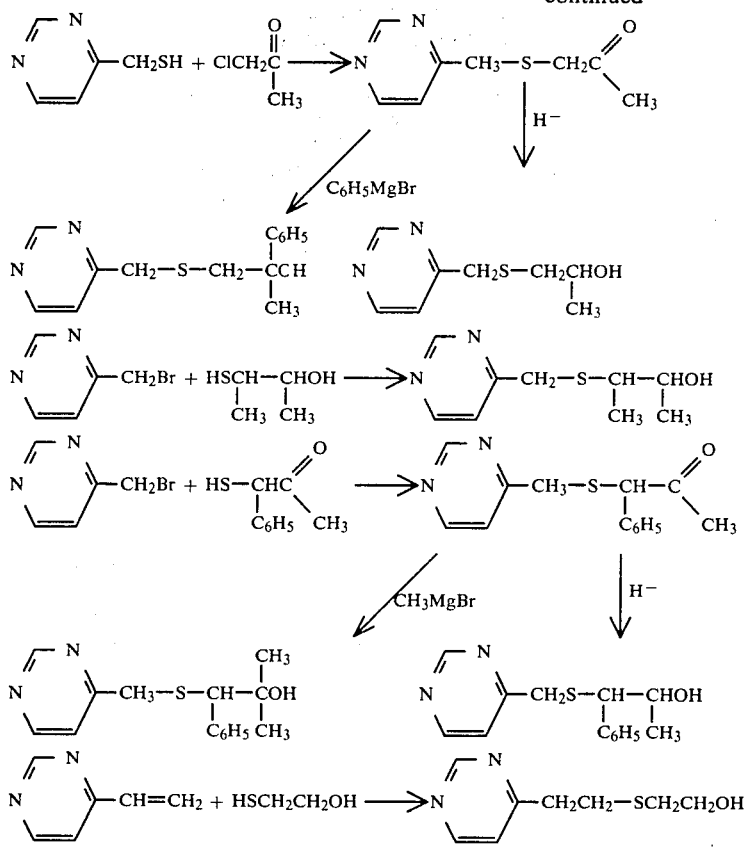

The pharmaceutically acceptable acid addition salts of the novel pyridines and pyrimidines are also embraced by the present invention and are readily prepared by contacting the free base with the appropriate mineral or organic acid in either aqueous solution or in a suitable organic solvent. The salt may then be obtained by precipitation or by evaporation of the solvent. The pharmaceutically acceptable acid addition salts of this invention include, but are not limited to, those formed with hydrochloric, hydrobromic, nitric, phosphoric, sulfuric, benzenesulfonic, citric, laurylsulfonic, fumaric, oxalic, maleic, methanesulfonic, tartaric, p-toluenesulfonic, and succinic acid. With polybasic acids, the salt can include more than one mole of base per mole of acid. However, the acid addition salts which are mole for mole are preferred. A salt of particular value in this invention is 4-(2-hydroxyethylthiomethyl)-pyridinium dihydrogen phosphate:

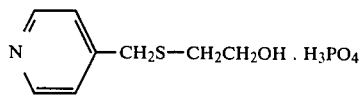

which is readily crystallized and purified, and has excellent water solubility, facilitating ready bioavailability.

As mentioned above, the immunoregulatory activity of the compounds of this invention is assessed by the mouse E-rosette procedure. In the mouse, the presence of a thymus is required for full expression of normal rosette formation with sheep erythrocytes [see for example, Bach and Dardenne, Immunol. 25, 353 (1973)]. The procedure examines the ability of a drug to restore azathioprine-sensitive, rosette-forming cells in adult thymectomized mice to the levels of normal animals. Specifically, rosette formation is examined in CD-1 mice thymectomized at 4 weeks of age and left at least 14 days post-surgery before manipulation (ATX mice). The ATX mice are dosed orally either with saline vehicle or drug. Sixteen hours later, single cell suspensions are prepared in Hanks balanced salt solution (HBSS) from the pooled spleens of three mice. To each tube is added 0.1 ml of lymphocytes ($6 \times 10^7$/ml) in HBSS and either 0.1 ml of HBSS or 0.1 ml of 40 $\mu$g/ml azathioprine in HBSS. After 90 minutes incubation at 37° C., the cells are washed 2× with 5 ml. of HBSS, made back up to 0.2 ml, and 0.2 ml of sheep red blood cells (erythrocytes) at $1.2 \times 10^8$ cells/ml. added. Then $\mu$l are pipetted on hemagglutination slides and the number of rosettes counted. The ability of the test compound to restore the number of azathioprine sensitive rosetting cells to normal or higher is determined. In normal mice 42%±12% azathioprine sensitivity is found. In adult thymectomized mice 3±3% azathioprine sensitivity is found. The ability of the compounds of the present invention to restore azathioprine sensitive rosetting cells to normal or above at various oral dosages (mg./kg., i.e. mg. of drug/kg. of mouse body weight) is shown in Table I. The higher the percentage and the lower the effective dosage, the more active is the compound as an immunoregulatory agent. In the same test, 4-(2-hydroxyethylthiomethyl)pyrimidine shows a 38% restoration of rosette formation at an oral dosage of 1 mg./kg.

Table I

Immunoregulatory Activity
Activity of Pyridine Derivatives in
the Mouse E-Rosetting Procedure
(Oral Dosage of 1 mg./kg.)

| Y | R$^1$ | n | % Rosetting Cells |
|---|---|---|---|
| —CH$_2$—CH$_2$— | H | 1 | 50, 43$^{a,b}$ |
| —CH—CH—<br>\|   \|<br>CH$_3$ CH$_3$ | H | 1 | 63 |
| —CH$_2$—CH—<br>\|<br>CH$_2$OH | H | 1 | 57 |
| (cyclohexyl) | H | 1 | 59 |
| —CH—CH$_2$—<br>\|<br>CH$_3$ | H | 1 | 40 |
| —CH—CH$_2$—<br>\|<br>C$_6$H$_5$ | H | 1 | 33 |
| —CH$_2$—CH—<br>\|<br>CH$_3$ | H | 1 | 56 |
| —CH$_2$—CH—<br>\|<br>C$_6$H$_5$ | H | 1 | 8, 39$^{a,c}$ |
| —CH$_2$—CH—<br>\|<br>(phenyl-OCH$_3$) | H | 1 | 43 |
| —CH$_2$—CH—<br>\|<br>(phenyl-NO$_2$) | H | 1 | 40 |
| —CH—CH—<br>\|   \|<br>CH$_3$ C$_6$H$_5$ | H | 1 | 33 |
|     CH$_3$<br>    \|<br>—CH$_2$—C—<br>    \|<br>    CH$_3$ | H | 1 | 39 |
| —CH$_2$CH$_2$CH$_2$— | H | 1 | 36 |
| —CH$_2$CH$_2$— | CH$_3$ | 1 | 33 |
| —CH$_2$CH$_2$— | CCH$_3$<br>\|\|<br>O | 1 | 40 |
| —CH$_2$CH$_2$— | H | 2 | 50 |
| Untreated controls (thymectomized mice) | | | 0–3 |

$^a$Separate results obtained in two tests.
$^b$60, 58 at 0.3 mg./kg.; 42, 53 at 0.3 mg./kg.; 42, 51 at 0.1 mg./kg.; 21, 33 at 0.03 mg./kg.; 16 at 0.01 mg./kg.
$^c$50 at 10 mg./kg.

As mentioned above, the antiinflammatory activity of the compounds of the present invention is determined in the standard carrageenin-induced rat foot edema test [described by C. A. Winter et al., *Proc. Soc. Exp. Biol.* 111, p. 544 (1962)]. In this test, antiinflammatory activity is determined as the inhibition of edema formation in the hind paw of male albino rats (weight 150–190 g.) in response to a subplantar injection of carrageenin. The carrageenin is injected as a 1 percent aqueous suspension (0.05 ml.) 1 hour after oral administration of the drug. Edema formation is then assessed 3 hours after the carrageenin injection by measuring the volume of the injected paw initially as well as at the 3 hour mark. The increase in volume three hours after carrageenin injection constitutes the individual response. Compounds are considered active if the response between the drug-treated animals (six rats/group) and the control group (i.e., animals receiving the vehicle alone) is deemed to be significant on comparison with results afforded by standard compounds like acetylsalicylic acid at 100 mg./kg of phenylbutazone at 33 mg./kg., both by the oral route of administration. The activity of the compound under test is expressed as the % inhibition of edema at a given oral dose. The ability of compounds to inhibit edema at various oral dosages (mg./kg., i.e. mg. of drug/kg. of rat body weight) is shown in Table II. The higher the % inhibition of edema and the lower the dose, the more active the compound. In the same test, 4-(2-hydroxyethylthiomethyl)pyrimidine shows an 11% inhibition of edema at 33 mg./kg.

Table II

Antiinflammatory Activity
Activity of Pyridines in
the Rat Foot Edema Procedure
(Oral Dosage of 33 mg./kg.)

| Y | R$_1$ | n | % Inhibition of Edema |
|---|---|---|---|
| —CH$_2$—CH$_2$— | H | 1 | 52$^a$ |
| —CH$_2$—CH—<br>\|<br>CH$_2$OH | H | 1 | 17 |
| —CH—CH$_2$—<br>\|<br>CH$_3$ | H | 1 | 20 |
| —CH$_2$—CH—<br>\|<br>CH$_3$ | H | 1 | 5 |

$^a$29 at 10 mg./kg.; 16 at 3.3 mg./kg.

The activity of 4-(2-hydroxyethylthiomethyl)pyridine (Y is —CH$_2$CH$_2$—; R$_1$ is H) in both the immunoregulatory and the antiinflammatory procedures (Tables I and II) is noteworthy. Furthermore, this compound does not inhibit prostaglandin synthesis in MC5-5 cells in vitro (IC$_{50}$>100 μM), and therefore does not share the prominent adverse side effect of many other nonsteroidal antiinflammatory (NSAI) drugs, i.e., ulcerogenicity. That 4-(2-hydroxyethylthiomethyl)pyridine is easily distinguishable from classical NSAI drugs is further demonstrated by its lack of activity in an ultraviolet light induced erythema procedure at a dose of 33 mg./kg. p.o., a procedure where indomethacin, phenylbutazone and other NSAI drugs cause clearcut suppression of erythema.

4-(2-Hydroxyethylthiomethyl)pyridine provides dose-related protection from the polyarthritis produced by injection of complete Freund's adjuvant in Wistar-Lewis rats. This agent is active in this procedure over a dose range of 3.3 to 33 mg./kg. p.o. and has an ED$_{50}$ value of approximately 33 mg./kg. Its antiarthritic effect is selective for the slow onset, lymphoid cell mediated, secondary response (the spread of disease to the uninjected foot) with no effects on the rapid onset, acute inflammation of the adjuvant-injected foot either on day 4 or on day 16. It does not affect the weight loss induced by adjuvant disease. Piroxicam and phenylbutazone, on the other hand, are effective in suppressing both the primary and secondary responses and in partially preventing the weight loss. This pattern of antiarthritic activity again distinguishes 4-(2-hydroxyethylthiomethyl)pyridine /from the classical NSAI drugs.

Four daily oral doses of 4-(2-hydroxyethylthiomethyl)pyridine at 33 mg./kg. did not affect the humoral immune response of mice to sheep red blood cells. Under the same conditions, the immunosuppressive drugs, methotrexate, cyclophosphamide, azathioprine and 6-mercaptopurine are profoundly inhibitory.

4-(2-Hydroxyethylthiomethyl)pyridine exhibits no significant ulcerogenic effects in rats at a dose of 100 mg./kg., p.o. Although a slight ulcerogenic tendency is observed for levamisole at 100 mg./kg. p.o., no statistically significant effect is produced. These results stand in marked contrast to those of phenylbutazone, aspirin and indomethacin where distinct ulcerogenic effects are seen at oral doses of 100, 50 and 10 mg./kg., respectively.

4-(2-Hydroxyethylthiomethyl)pyridine is less acutely toxic than levamisole in rats and mice. Its oral $LD_{50}$ in mice is greater than 100 mg./kg. In the rat, it also has an $LD_{50}$ value greater than 1000 mg./kg. Administered orally by capsule (unformulated) for fourteen days to dogs at a dose of 30 mg./kg./day, it caused no abnormalities in gross pathology and histopathology. No changes in clinical chemistry, hematology or body weight were observed.

The novel pyridines and pyrimidines of this invention and their pharmaceutically acceptable acid addition salts are useful therapeutically as antiinflammatory agents or as regulants of the immune response in warm-blooded animals. The combination of antiinflammatory activity and immune regulant activity is particularly valuable in the treatment of conditions such as rheumatoid arthritis and other diseases associated with immune deficiency and accompanied by inflammation. Thus, compounds of the present invention act to relieve the pain and swelling associated with such conditions while also regulating the immune response of the subject and thereby alleviating the underlying immune disorder by maintaining immune competence. Accordingly, the present invention embraces a method of inhibiting inflammatory reactions or regulating the immune response in a warm-blooded animal by administering to the subject a pyridine or pyrimidine of the present invention, or a pharmaceutically acceptable acid addition salt thereof, in an amount sufficient to inhibit the inflammatory reactions or regulate the immune response. In accord with this method, the compounds of the present invention may be administered to the subject in need of treatment by conventional routes, such as orally or parenterally, at dosages in the range of about 0.10 to about 50 mg./kg. body weight of the subject per day, preferably about 0.10 to about 10 mg./kg. body weight per day administered singly or as a divided dose. However, the optimum dosage for the individual subject being treated will be determined by the person responsible for treatment, generally smaller doses being administered initially and thereafter gradual increments made to determine the most suitable dosage. This will vary according to the particular compound employed and with the subject being treated.

The compounds can be used in pharmaceutical preparations containing the compound, or a pharmaceutically acceptable acid addition salt thereof, in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like may be used, as well as aqueous solutions of water-soluble pharmaceutically acceptable acid addition salts of the compounds. The injectable solutions prepared in this manner can then be administered intravenously, intraperitoneally, subcutaneously or intramuscularly, with intravenous and intramuscular administration being preferred. For localized treatment of inflammation the compounds can also be administered topically in the form of ointments, creams, pastes and the like in accord with conventional pharmaceutical practice.

The present invention is illustrated by the following examples. However, it should be understood that the invention is not limited to the specific details of these examples.

EXAMPLE 1

4-(2-Hydroxyethylthiomethyl)pyridine (A) Under a nitrogen atmosphere, sodium methoxide (170.1 g., 3.15 moles, 2.1 equiv.) was dissolved in 2.7 l. of absolute ethanol, and the stirred solution cooled in an ice bath. Solid 4-picolyl chloride hydrochloride (97%, 253.6 g., 1.5 moles, 1 equiv.) was added portionwise over approximately 15 minutes. A solution of 2-mercaptoethanol (128.9 g., 1.65 moles), dissolved in 300 ml. of ethanol, was then added dropwise over approximately 30 minutes. The reaction was allowed to warm to room temperature and stirred for 21.5 hours. Diatomaceous earth was added to the reaction mixture, which after brief stirring, was filtered. The filter cake was repulped 2×1500 ml. of absolute ethanol, the filtrates were combined with the original filtrate, and the combined ethanol solution evaporated to a solid-containing oil (approximately 290 g.). The oil was dissolved in 1500 ml. of hot chloroform, treated with activated carbon, filtered, reconcentrated to oil (274 g.) and chromatographed on 1.5 kg. of silcia gel in a 10 cm. diameter column using chloroform as eluant. Fractions of approximately 3.5 l. were taken. Fractions 3 to 18 were combined, concentrated to oil, taken up in approximately 1 l. of ethyl acetate and evaporated to yield relatively pure 4-(2-hydroxyethylthiomethyl)pyridine [195.7 g., ir (film): 3.17, 3.51, 3.58, 6.27, 9.45 and 12.27μ; pnmr/CDCl$_3$/TMS/δ: 8.63–8.42 (m, 2H), 7.38–7.18 (m, 2H), 3.73 (t, 2H), 3.72 (s, 2H), 2.98 (s, broad, 1H) and 2.63 (t, 2H) ppm]. On standing, product prepared by this procedure slowly crystallized (m.p. 47°–48° C.).

The dihydrogen phosphate salt was prepared as follows. The free base (freshly prepared oil, 195.7 g., 1.16 moles) was dissolved in 488 ml. of ethyl acetate and cooled in an ice bath. A solution of aqueous phosphoric acid (85.5%, 132.5 g., 1.16 moles) in 488 ml. of ethyl acetate was added dropwise over approximately 10 minutes to the stirred solution of the free base. The dihydrogen phosphate salt precipitated during this addition as an oil/solid mixture. Complete crystallinity was achieved by removing the slurry from the ice bath, adding 687 ml. of methanol and stirring. Filtration gave crude dihydrogen phosphate salt (274.5 g.). Recrystallization from approximately 7 l. hot absolute ethanol, dissolved hot and filtered, evaporated to approximately 5.5 l. and cooled) gave purified 4-(2-hydroxyethylthiomethyl)pyridinium dihydrogenphosphate [228.9 g.; m.p. 96.5°–98.5° C.; ir (KBr): 3.00, 3.57, 6.12, 7.75, 9.44µ; pnmr/DMSO-d$_6$/TMS/δ: 8.73–8.33 (m, 6H, 4H exchange with D$_2$O), 7.53–7.25 (m, 2H), 3.80 (s, 2H), 3.55 (t, 2H) and 2.52 (t, 2H), ppm].

Analysis: Calcd.: C$_8$H$_{11}$NOS.H$_3$PO$_4$: C, 35.96; H, 5.28; N, 5.24; P, 11.59. Found: C, 35.61; H, 5.03; N, 5.08; P, 11.71.

Highly purified free base (m.p. 48°–49° C.) was regenerated from the phosphate salt by dissolving the salt in water, making the solution basic with sodium hydroxide, extracting the free base into chloroform and evaporating to dryness.

(B) In an alternative procedure, 2-mercaptoethanol (11.9 g., 0.152 mole) was dissolved in 138.5 ml. of absolute ethanol and cooled to 18° C. Sodium methoxide (15.7 g., 0.291 mole) was added; the temperature rose to 38° C. and a clear solution resulted. The reaction mixture was cooled somewhat and, while maintaining the temperature below 30° C., 4-picolyl bromide hydrobromide (35 g., 0.138 moles) was added portionwise over 10 minutes. The reaction mixture was then heated to reflux and refluxed for 80 minutes. The reaction was concentrated to a thick mass, which was dissolved in 140 ml. of water and extracted twice with 140 ml. of ethyl acetate. Salt was dissolved in the aqueous phase during the second extraction. The combined ethyl acetate extracts were back washed twice with 150 ml. of 1 N NaOH, dried over anhydrous magnesium sulfate, filtered, and concentrated to about half-volume. While maintaining the temperature between 30° and 35° C., phosphoric acid (12.0 g., 0.122 moles) was added very slowly to directly precipitate crude product as the dihydrogen phosphate salt, recovered by filtration after stirring for 1 hour. The crude was recrystallized from absolute ethanol, yielding purified 4-(2-hydroxyethylthiomethyl)pyridinium dihydrogen phosphate (14.0 g.).

EXAMPLE 2

4-(3-Hydroxy-2-butylthiomethyl)pyridine

Sodium methoxide (3.40 g., 63 mmoles) was dissolved in 30 ml. of absolute ethanol under nitrogen and cooled in an ice bath. To the chilled solution there was added a suspension of finely ground 4-picolyl chloride hydrochloride (5.07 g., 30 mmoles) suspended in approximately 30 ml. of absolute ethanol over 15 minutes, followed by the addition of a solution of 3-mercapto-2-butanol [3.19 g., 30 mmoles, Price et al., J. Am. Chem. Soc. 75, 2396 (1953)] in 6 ml. of absolute ethanol over 5 minutes. The reaction mixture was warmed to room temperature and allowed to stir for 14 hours. The reaction mixture was filtered, the solids being extracted with additional ethanol. The ethanol solutions were combined and evaporated to an oil containing solids (6.31 g.), which was taken up in chloroform, solids removed by filtration and concentrated to an oil. The resuling oil was chromatographed on 200 g. of silica gel with chloroform as eluant. Product fractions were combined and stripped to an oil (5.03 g.). Dissolution in approximately 50 ml. of ethyl acetate, filtration through diatomaceous earth and removal of solvent gave purified 4-(3-hydroxy-2-butylthiomethyl)pyridine [oil; ir (film: 3.08, 3.40, 3.45, 6.24, 7.08, 9.20, 12.27µ; m/e calcd: 197, found: 197; pnmr/CDCl$_3$/TMS/δ: 8.57 (m, 2H), 7.30 (m, 2H), 3.85 (m, 1H), 3.76 (s, 2H), 3.12 (s, broad, 1H, exchanges with D$_2$O), 2.75 (m, 1H) and 1.20 (d, 6H)].

Analysis: Calcd: C$_{10}$H$_{15}$NOS: C, 60.88; H, 7.66; N, 7.10 Found: C, 60.81; H, 7.77; N, 7.18.

EXAMPLE 3

4-(2,3-Dihydroxy-1-propylthiomethyl)pyridine

Sodium methoxide (3.24 g., 60 mmoles) was dissolved in 36 ml. of absolute ethanol under a nitrogen atmosphere and the stirred solution cooled in an ice bath. With continued cooling, finely divided 4-picolyl chloride hydrochloride (5.07 g., 30 mmoles), slurried in approximately 35 ml. of absolute ethanol, was added over 15 minutes, followed by a solution to 3-mercapto-1,2-propanediol (3.24 g., 30 mmoles) in 6 ml. of absolute alcohol added dropwise over approximately 5 minutes. The reaction mixture was left to warm to room temperature and stirred overnight (16 hours). The reaction mixture was clarified by filtration through diatomaceous earth; the insolubles and the diatomaceous earth were extracted with ethanol, the original filtrate combined with the extract, and the whole concentrated to an oil (5.83 g.). Vacuum distillation, which appeared to produce considerable degradation, gave approximately 2.0 ml. of reasonably pure product (b.p. 230° C./0.3 mm.). The distillate was taken up in cold methanol, a solid impurity removed by filtration, and purified 4-(2,3-dihydroxy-1-propylthiomethyl)pyridine recovered by evaporating the filtrate to an oil (2.15 g.; ir (film): 2.97, 3.46, 3.50, 6.21, 7.05, 9.40 and 12.25µ).

Analysis: Calcd.: C$_9$H$_{13}$NO$_2$S: C, 54.25; H, 6.58; N, 7.03. Found: C, 54.11; H, 6.39; N, 7.31.

EXAMPLE 4

4-(2-Hydroxyphenylthiomethyl)pyridine

Sodium methoxide (2.16 g., 40 mmoles) was dissolved in 24 ml. of absolute alcohol, stirring under nitrogen and the solution was cooled in an ice bath. 4-Picolyl chloride hydrochloride (3.38 g., 20 mmoles), finely divided and suspended in approximately 20 ml. of absolute ethanol, was added dropwise over approximately 15 minutes. A solution of 2-mercaptophenol (2.52 g., 20 mmoles) in 4 ml. of absolute ethanol was then added over approximately 5 minutes. The reaction mixture was warmed slowly and left to stir under nitrogen for 14 hours at room temperature. The reaction was filtered with diatomaceous earth. Solids were repulped with an additional 75 ml. of ethanol. The ethanol filtrates were combined and concentrated to yield crude product as a solid (2.02 g.). Recrystallization from aqueous ethanol gave purified 4-(2-hydroxyphenylthiomethyl)pyridine (1.24 g., m.p. 142°–145° C.).

Analysis: Calcd.: C$_{12}$H$_{11}$NOS: C, 66.33; H, 5.10; N, 6.45; m/e 217. Found: C, 66.23; H, 5.19; N, 6.43; m/e 217.

By following the methodology of Examples 1–4, 4-picolyl chloride hydrochloride is reacted with ethyl mercaptoacetate to yield ethyl 4-picolythioacetate (preferably with substitution of an equivalent amount of sodium ethoxide for sodium methoxide), with 2- methoxyethylmercaptan [Chapman et al., J. Chem. Soc. 579 (1950)] to yield 4-(2-methoxyethylthiomethyl)pyridine, with 1-mercapto-2-propanol [Sjoberg, Ber. 75, 13 (1942)] to yield 4-(2-hydroxy-1-propylthiomethyl)pyridine, with 1-phenyl-1-mercaptoacetone [von Wacek et al., Ber. 75, 1353 (1942)] to yield 1-(4-picolylthio)-1-phenylacetone, and with mercaptoacetone to yield 4-picolylthioacetone.

Furthermore 4-picolyl chloride hydrochloride or 4-picolyl bromide hydrobromide is converted to the free base by rendering the salt basic in ethanol, and then reacting with sodium or potassium cyanide (1.05 equivalents) to form the corresponding nitrile. The nitrile is solvolized in ethanol with aqueous hydrochloride acid to form ethyl 4-picolylacetate [cf. Rising et al., J. Am. Chem. Soc. 50, 1211 (1928)]. The latter is reduced with Red-al in benzene-tetrahydrofuran and isolated by the method of Examples 9 and 10, yielding 2-(4-pyridyl)ethanol. The alcohol is converted to corresponding chloride by reaction with thionyl chloride in refluxing methylene chloride [cf. Gilman et al., Rec. trav. chim. 51, 93 (1932)]. The 2-(4-pyridyl)ethyl chloride hydrochloride which forms is isolated by evaporation.

Using the procedures of Examples 1 to 4, 2-(4-pyridyl)ethyl chloride is reacted with 2-mercaptoethanol to yield 4-[2-(2-hydroxyethylthio)ethyl]pyridine, with 3-mercapto-2-butanol to yield 4-[2-(3-hydroxy-2-butylthio)ethyl]pyridine, with 3-mercapto-1,2-propanediol to yield 4-[2-(2,3-dihydroxy-1-propylthio)ethyl]pyridine, with 2-mercaptophenol to yield 4-[2-(2-hydroxyphenylthio)ethyl]pyridine, with methyl mercaptoacetate (preferably in methanol rather than ethanol solution) to yield methyl 2-[2-(4-pyridyl)ethylthio]acetate and with mercaptoacetone to yield 2-(4-pyridyl)ethylthioacetone.

EXAMPLE 5

Sodium 2-(-Picolylthio)propionate

Sodium methoxide (5.1 g., 94 mmoles) was dissolved in 50 ml. of absolute ethanol and cooled in an ice bath. A slurry of 4-picolyl chloride hydrochloride (5.0 g., 30.4 mmoles) in 45 ml. of ethanol was added and the chilled reaction mixture stirred for approximately 10 minutes. Finally, 2-mercaptopropionic acid (3.23 g., 30.4 mmoles) dissolved in 5 ml. of ethanol was added over a 10 minute period. The mixture was allowed to warm to room temperature and stirred overnight (approximately 16 hours). The reaction was filtered through filter aid to remove salts, carbon treated and concentrated to crude sodium 2(4-picolylthio)propionate (approximately 7 g. of oil used directly in the next step).

EXAMPLE 6

Sodium Phenyl(4-picolylthio)acetate

Sodium methoxide (6.8 g., 0.124 mole) was dissolved in 150 ml. of ethanol and cooled to 0° C. A solution of alpha-mercaptophenylacetic acid (7.0 g., 0.042 moles) in 50 ml. of ethanol was added over a period of 5 minutes to the cold methoxide solution. After 5 minutes, a slurry of 4-picolylchloride hydrochloride (6.83 g., 0.042 moles) slurried in 50 ml. of ethanol was then added over 5 minutes. The reaction was removed from the ice bath and left to stir for approximately 60 hours. The reaction mixture was filtered and evaporated to yield sodium phenyl(4-picolylthio)acetate (11.8 g.; waxy solid; ir: 3.0, 6.1, 6.25, 7.3, 13.6μ) used directly in the next step.

By the method of Examples 5 and 6, 4-picolyl chloride hydrochloride is reacted with mercaptoacetic acid to yield sodium 2-(4-pyridylmethylthio)acetate.

EXAMPLE 7

Ethyl 2-(4-Picolylthio)propionate

Crude sodium 2-(4-pyridylmethylthio)propionate (approximately 7 g.) was taken up in 100 ml. of absolute ethanol and approximately 5 cc. of 3 A molecular sieves were added. Dry hydrogen chloride was bubbled into the reaction mixture, which was refluxed for 75 minutes, while continuing to saturate with hydrogen chloride during the initial 15 minutes. The mixture was cooled to room temperature and allowed to stir overnight (approximately 16 hours). The mixture was filtered through diatomaceous earth and concentrated to a semi-solid mixture. The esterification step was repeated on this mixture, except saturation with hydrogen chloride was continued during 1 hour of reflux and refluxing was continued overnight. The reaction mixture was cooled to room temperaure, filtered through diatomaceous earth and evaporated to an oil. The oil was extracted with chloroform, leaving filterable salts behind, and the chloroform stripped to yield ethyl 2-(4-picolylthio)propionate (waxy solid; ir (KBr) 3.0, 3.5, 5.75, 6.15, 6.30, 6.70, 8.6, 12.25μ; m.s.: m/e calcd: 225, found: 225, 152, 124, 102, 92, 45).

Using the same ethanolic hydrogen chloride procedure, sodium picolylthioacetate is converted to ethyl 4-picolylthioacetate.

EXAMPLE 8 methyl Phenyl-4-pyridylmethylthioacetate

Sodium phenyl (4-pyridylmethylthio)acetate was dissolved in methanol and dry hydrogen chloride added slowly so as to maintain gentle reflux for 1 hour. After cooling and stirring for approximately 16 hours, the reaction mixture was filtered and concentrated to yield methyl phenyl (4-pyridylmethylthio)acetate (11.6 g.; oil; ms, calcd: m/e 273; found: 273, 214, 150 136, 124, 121, 105, 77, 65).

The corresponding ethyl and propyl esters are prepared by the same method, substituting ethanol and propanol, respectively, for methanol.

By the same method, sodium 4-picolylthioacetate is converted to methyl 4-picolylthioacetate.

EXAMPLE 9

4-(1-Hydroxy-2-propylthiomethyl)pyridine

Red-al [70% solution of sodium bis(2-methoxyethyl)aluminum hydride in benzene, 1.2 g., 1.1 ml., 5.86 mmoles] was cooled under nitrogen in an ice bath. A solution of ethyl 2-(4-pyridylmethylthio)propionate in 10 ml. of dry tetrahydrofuran was added dropwise over 10 minutes. The mixture was then heated and gently refluxed for 1 hour and then stirred at room temperature for approximately 16 hours. The reaction mixture was poured into 40 ml. of ice cold 1 N HCl and salts removed by filtration. The filtrate was made basic with sodium bicarbonate and the product extracted into ethyl acetate (four times with 50 ml. aliquots). The combined ethyl acetate extracts were dried (by wash with saturated sodium chloride and then over anhydrous sodium sulfate) and concentrated to yield 4-(1-hydroxy-2-propylthiomethyl)pyridine (oil; approximately 200 mg.; pnmr/CDCl$_3$/TMS/τ: 8.6 (d, 3H), 7.2

(s, broad, 1H), 6.3 (m, 5H), 2.7 (d, 2H), 1.5 (d, 2H); m/e calcd: 183; found: 183, 152, 118, 92, 65; ir (film): 3.1, 6.25, 7.1, 9.25, 12.25µ). To further purify the product, it was taken up in chloroform, treated with activated carbon and concentrated to an oil (194 mg.).

EXAMPLE 10

4-(1-Phenyl-2-hydroxyethylthiomethyl)pyridine

Crude methyl phenyl (4-pyridylmethylthio)acetate (5 g., 0.018 mole) was dissolved in 30 ml. of toluene and added dropwise to 7.4 ml. of stirred, cold Red-al [70% solution of sodium bis(2-methoxyethoxy)aluminum hydride in benzene] previously cooled in an ice bath. After foaming ceased, the reaction was warmed to room temperature and stirred for approximately 16 hours. To isolate the product, the reaction was poured into approximately 60 ml. of cold 1 N hydrochloric acid, precipitated salts removed by filtration, the filtrate made slightly basic with sodium bicarbonate, decanted away from precipitated salts, and the product extracted into excess toluene. The basic salts were extracted with hot ethyl acetate. The toluene and ethyl acetate extracts were combined, dried over anhydrous magnesium sulfate and concentrated to an oil (2.05 g.). The oil was chromatographed on 110 g. of silica gel with 1:1 hexane:ethyl acetate as eluent. Fractions of approximately 10 ml. each were taken and the chromatography followed by thin layer chromatography (silica gel eluted with ethyl acetate). Product fractions (which eluted after three impurity bands) showed Rf ca. 0.25 in the thin layer system. Product fractions were combined and evaporated to yield methyl phenyl(4-pyridylmethylthio)acetate (oil; anal. calcd. for $C_{14}H_{15}NOS.0.25H_2O$: C, 67.39; H, 6.21; N, 5.60; m/e, 245; found: C, 67.57; H, 6.30; N, 5.32; m/e, 245; other mass spectra peaks: 214, 136, 121, 103, 92, 91, 77 and 45).

The yield of product is improved by employing purified starting ester.

The Red-al reduction procedure of Examples 9 and 10 is used to reduce either methyl or propyl phenyl-4-pyridylmethylthioacetate to 4-(1-phenyl-2-hydroxyethylthiomethyl)pyridine, ether methyl or ethyl 4-picolylthioacetate to 4-(2-hydroxyethylthiomethyl)-pyridine, 1-(4-picolylmethylthio)-1-phenylacetone to 4-(1-phenyl-2-hydroxy-1-propylthiomethyl)pyridine, ethyl 2-(4-pyridyl)ethylthioacetate to 4-[2-(2-hydroxyethylthio)ethyl]pyridine, ethyl 2-[2-(4-pyridyl)ethylthio]propionate to 4-[2-(2-hydroxy-2-propylthio)ethyl]-pyridine and methyl 2-phenyl-2-[2-(4-pyridyl)ethylthio]acetate to 4-[2-(1-phenyl-2-hydroxyethylthio)ethyl]-pyridine.

EXAMPLE 11

4-Picolythioacetone

Under a nitrogen atmosphere, sodium methoxide (2.6 g., 48 mmoles) was dissolved in 40 ml. of ethanol and cooled in an ice bath. 4-Picolyl mercaptan (6.0 g., 48 mmoles) in 40 ml. of ethanol was added over 5 minutes, followed by the addition of chloroacetone (4.5 g., 48 mmoles) in 25 ml. of ethanol over 5 minutes. After stirring for an additional 15 minutes at 0°-5° C., the reaction mixture was allowed to warm to room temperature and stirred for approximately 65 hours. To isolate the product, the reaction was filtered through diatomaceous earth and the mother liquor evaporated to yield crude product as an oil (8.3 g.). The entire crude was chromatographed on 480 g. of silica gel with chloroform as eluant. Once the desired product began to come off the column, 2% methanol was added to the chloroform eluant. Product fractions were combined and concentrated to an oil. Finally dissolution in ethyl acetate, drying over anhydrous magnesium sulfate and reconcentrating gave purified 4-picolylthioacetone (4.91 g., m/e calcd.: 181, found: 181, 138, 124, 92, 65, 43; ir (KBr): 5.8, 6.2, 7.05, 12.25µ).

EXAMPLE 12

Alpha-(4-Picolylthio)acetophenone

Under a nitrogen atmosphere, sodium methoxide (0.81 g., 15 mmoles) was dissoled in 17.9 ml. of stirring absolute ethanol, and cooled in an ice bath. 4-Picolyl mercaptan (1.88 g., 15 mmoles) in 3 ml. of absolute ethanol was added dropwise over approximately 5 minutes, followed by alpha-bromoacetophenone (3.05 g., 15 mmoles) in 10 ml. of warm absolute ethanol added over approximately 10 minutes. The stirring reaction mixture was warmed to room temperature and left to stir for 17 hours. Salts were removed by filtration through diatomaceous earth, and the solids repulped for 0.5 hour with additional ethanol and refiltered. The ethanol filtrates were combined and concentrated to yield a waxy solid. The waxy solid was taken up in approximately 11 volumes of diethyl ether, treated with activated carbon, filtered and the mother liquor concentrated to a solid (1.90 g.). Recrystallization from diethyl ether/hexane gave purified alpha-(4-picolylthio)acetophenone (1.25 g. in two crops, m.p. 55°-59° C., ir (KBr): 5.92, 6.18, 7.00, 7.76, 9.78, 12.38, 13.70µ).

Analysis: Calcd.: $C_{14}H_{13}ONS$: C, 69.11; H, 5.39; N, 5.76; m/e 243. Found: C, 69.07; H, 5.47; N, 5.70; m/e 243.

Yields are improved by combining the ether dissolution-carbon treatment-concentration step with the ether-hexane recrystallization step.

EXAMPLE 13

Alpha-(4-Picolylthio)-p-methoxyacetophenone

Under a nitrogen atmosphere sodium methoxide (0.62 g., 11.4 mmoles) was dissolved in approximately 15 ml. of absolute ethanol and cooled in an ice bath. 4-Picolyl mercaptan (1.43 g., 11.4 mmoles) in approximately 3 ml. of absolute ethanol was added over approximately 5 minutes. After stirring for an additional 10 minutes, a slurry of alpha-bromo-p-methoxyacetophenone (2.62 g., 11.4 mmoles) in approximately 5 ml. of absolute ethanol was added over 10 minutes. The mixture was allowed to warm to room temperature and stirred for approximately 16 hours. The reaction mixture was concentrated to an oil containing solids, triturated with chloroform, salts removed by filtration and reconcentrated to an oil (3.6 g.). The oil was chromatographed on 120 g. of silica gel with chloroform as eluant. Product containing fractions were combined and stripped to an oil which crystallized on trituration with cold ether. Filtration gave alpha (4-picolythio)-p-methoxyacetophenone [2.27 g.; m.p. 64°-65° C.; ir (KBr): 3.14 3.5, 5.95, 6.25, 7.95, 8.55, 12.0 and 12.2µ; mass spectra: m/e calcd: 273, found: 273, 150, 135, 124, 107, 92; pnmr/CDClhd 3/TMS/τ: 6.35 (s, 2H), 6.3 (s, 2H), 6.1 (s, 3H), 3.1 (d, 2H), 2.7 (d, 2H), 2.0 (d, 2H), 1.4 (d, 2H)].

EXAMPLE 14

Alpha-(4-Picolythio)-p-nitroacetophenone

Under a nitrogen atmosphere, sodium methoxide (0.52 g., 9.6 mmoles) was dissolved in 15 ml. of absolute ethanol and cooled to 0°–5° C. 4-Picolyl mercaptan (1.2 g., 9.6 mmoles) in 15 ml. of ethanol was added over 5 minutes time. Alpha-bromo-p-nitroacetophenone (2.3 g., 9.6 mmoles) in 20 ml. of warm ethanol was then added over 5 minutes, the mixture was warmed to room temperature and left to stir for approximately 16 hours. The reaction mixture was filtered and the filtrate concentrated to an oil (4.3 g.). The oil was chromatographed on 175 g. of silica gel with 1:1 hexane:ethyl acetate as eluant. Product-containing fractions were combind and evaporated to yield alpha-(4-picolythio)-p-nitroacetophenone [1.40 g.; oil; pnmr/CDCl$_3$/TMS/$\tau$: 6.5 (3, 4 H), 2.7 (d, 2 H), 1.9 (d, 4 H), 1.5 (d, 2 H); mass spectra: m/e calcd.: 288; found: 288, 242, 165, 150, 138, 124, 104, 92, 76, 54, 39; ir (film): 3–3.5, 5.95, 6.25, 6.55, 7.35, 7.85, 11.70$\mu$].

EXAMPLE 15

Alpha-(4-Picolylthio)propionphenone

Under a nitrogen atmosphere, sodium methoxide (0.60 g., 11 moles) was dissolved in approximately 15 ml. of stirring ethanol and cooled in an ice bath. 4-Picolyl mercaptan (1.4 g., 11 mmoles) in approximately 3 ml. of absolute ethanol was added over 5 minutes and the mixture stirred for 15 minutes. Alphabromopropionphenone (2.4 g., 11 mmoles) in approximately 15 ml. of absolute ethanol was then added over 5 minutes. The reaction mixture was warmed to room temperature and stirred for approximately 16 hours. The reaction mixture was filtered and the filtrate evaporated to an oil, which was chromatographed on 100 g. of silica gel, with chloroform as eluant, to yield purified alpha-(4-picolylthio)-propiophenone [2.17 g.; oil; ir (CHCl$_3$): 3.5, 6.0, 6.25, 6.95, 7.05, 10.55; mass spectra: m/e calcd.: 257, found: 251, 197, 152, 134, 105; pnmr/CHCl$_3$/TMS/$\tau$: 8.5 (d, 3H), 6.4 (s, 2H), 5.7 (q, 1H), 2.8, 2.6, 2.1, 1.5 (all multiplets, 9H)].

By following the method of Examples 11–15, 4-picolyl mercaptan is reacted with 2-chloroethanol, 2-bromoethanol or ethylene oxide to yield 4-(2-hydroxyethylthiomethyl)pyridine, with 2-bromo-1-propanol to yield 4-(2-hydroxy-1-propylthiomethyl)pyridine, with 1-chloro-2-propanol to yield 4-(1-hydroxy-2-propylthiomethyl)pyridine, with bromoacetaldehyde diethyl acetal (followed by acid catalyzed hydrolysis) to yield 4-picolylthioacetaldehyde, with 3-bromo-2-butanol to yield 4-(3-hydroxy-2-butylthiomethyl)pyridine, with ethyl 2-bromoacetate to yield ethyl 4-picolylthioacetate, with ethyl 2-chloropropionate to yield ethyl 2-(4-picolylthio)acetate and with methyl 2-phenyl-2-bromoacetate to yield methyl phenyl(4-picolylthio)acetate.

Furthermore, by following this method 2-(4-pyridyl)ethyl mercaptan is reacted with 2-bromoethanol to yield 4-[2-(2-hydroxyethylthio)ethyl]pyridine, with 2-bromo-1-propanol to yield 4-[2-(2-hydroxy-1-propylthio)ethyl]pyridine, with 3-bromo-2-butanol to yield 4-[2-(3-hydroxy-2-butylthio)ethyl]pyridine, with ethyl 2-chloropropionate to yield ethyl 2-[2-(4-pyridyl)ethylthio]propionate, with methyl 2-phenyl-2-bromoacetate to yield methyl 2-phenyl-2-[2-(4-pyridyl)ethylthio]acetate, with alpha-bromoacetophenone to yield alpha-[2-(4-pyridyl)ethylthio]acetophenone, and with chloroacetone to yield 2-(4-pyridyl)ethylthioacetone.

EXAMPLE 16

4-(2-Hydroxy-1-propylthiomethyl)pyridine

Under a nitrogen atmosphere, 4-picolylthioacetone (9.10 g., 50 mmoles) was dissolved in 130 ml. of stirring isopropyl alcohol. Sodium borohydride (0.76 g., 20 mmoles, 1.6 equiv.) was added carefully in portions. A small amount of foaming occurred. The reaction was placed under nitrogen and heated to reflux for 1.5 hours. The reaction was cooled and concentrated to an oil. The oil was stirred and cooled in an ice-bath and 150 ml. of 4 N hydrochloric acid added slowly, so as to control the foaming which resulted. The solution was stirred for a further 15 minutes and then made strongly basic by the addition of 10 N sodium hydroxide. The oil which formed on basification was extracted into chloroform (three 250 ml. portions), with dilute sodium hydroxide backwash of the combined chloroform layers. The chloroform solution was dried over anhydrous sodium sulfate and evaporated to yield 4-(2-hydroxy-1-propylthiomethyl)pyridine [8.71 g.; oil; pnmr/CDCl$_3$/TMS/$\delta$: 8.57 (m, 2H), 7.28 (m, 2H), 3.90 (sextet, 1H), 3.87 (s, 1H, exchanges with D$_2$O), 3.72 (s, 2H), 2.52 (d, 2H) and 1.23 (d, 3H)].

The hydrochloride salt was obtained as an oil by dissolving 0.367 g. (2 mmole) of the free base in 2 ml. of 1 N hydrochloric acid (2 mmole) and evaporation of solvent.

The dihydrogen phosphate salt was prepared by dissolving free base (5.00 g., 27.3 mmoles) in 11.6 ml. of ethyl acetate, cooling the solution to 0° C., adding 85.5% phosphoric acid (3.13 g., 27.3 mmoles) in 11.6 ml. of ethyl acetate. The salt precipitated as a gummy solid. Methanol (100 ml.) was added, the mixture warmed to a clear solution, and concentrated to an oil which crystallized on standing. Recrystallization from isopropyl alcohol gave purified dihydrogen phosphate salt [3.78 g.; m.p. 88°–91° C.; ir (KBr): 2.95, 3.55, 6.10, 6.65$\mu$; pnmr/(CD$_3$)$_2$SO/TMS/$\delta$: 8.57 (m, 2H), 8.33 (s, 4H, exchanges with D$_2$O), 3.80 (s, 2H, 3.77 (sextet, 1H), 2.44 (d, 2H) and 1.10 (d, 3H)].

Analysis: Calcd.: C$_9$H$_{13}$NO$_3$.H$_3$PO$_4$: C, 38.4; H, 5.7; N, 5.0; m/e 183. Found: C, 38.6; H, 5.3; N, 5.2; m/e 183.

EXAMPLE 17

4-(2-Hydroxy-2-phenylethylthiomethyl)pyridine

Under a nitrogen atmosphere, alpha-(4-picolylthio)acetophenone (852 mg., 3.5 mmoles) was dissolved in 8.75 ml. of isopropyl alcohol. Sodium borohydride (54 mg., 1.4 mmoles, 1.6 equiv.) was added. After stirring for 0.5 hour at room temperature, the reaction mixture was refluxed for 1 hour. The reaction mixture was cooled somewhat and then evaporated to an oil. With stirring, hydrochloric acid (4 N, 10 ml.) was added slowly to the oil, so as to control heating and foaming. Once addition was complete and there was no evidence of gas evolution, the acid solution was made strongly basic with 20% sodium hydroxide. The oil which precipiated was extracted into chloroform. The chloroform was back-washed with dilute sodium hydroxide, dried over anhydrous sodium sulfate and concentrated to an oil (0.87 g.) which crystallized to a waxy solid on standing. The solid was triturated with ether and filtered to yield crude product (0.61 g.). Recrystallization from ethyl acetate gave purified 4-(2-hydroxy-2-phenylethylthiomethyl)pyridine [0.42 g.; m.p. 116.5°–119° C. (incomplete); ir (KBr): 3.17, 5.1–5.8, 6.22, 6.88, 9.49, 12.25, 13.88 and 14.25μ; mass spectra: m/e calcd.: 245, found: 245; pnmr/CDCl₃/TMS/δ: 8.73–8.37 (m, 2H), 7.57–7.10 (m, 7H), 4.75 (t, 1H), 3.63 (s, 2H), 3.10 (s, 1H, exchanges with D₂O) and 2.72 (d, 2H)].

EXAMPLE 18

4-[2-(4-Methoxyphenyl)-2-hydroxyethylthiomethyl]-pyridine

Under a nitrogen atmosphere, alpha-(4-picolylthio)p-methoxyacetophenone (1.99 g., 7.3 mmoles) was dissolved in 25 ml. of stirring ethanol. Sodium borohydride (0.45 g., 11.7 mmoles) was added portionwise and the mixture then refluxed gently for 30 minutes. The mixture was partially cooled and evaporated to dryness. Water (50 ml.) was added to the residue, which was then acidified with excess 1 N hydrochloric acid. The acid solution was made basic with solid sodium bicarbonate and product extracted into ethyl acetate. The ethyl acetate was dried over anhydrous sodium sulfate and concentrated to an oil, which crystallized on standing. Trituration with diethyl ether and filtration gave purified 4-[2-(4-methoxyphenyl)2-hydroxyethylthiomethyl]pyridine [1.50 g.; m.p. 70°–72.5° C.; pnmr/CDCl₃/TMS/τ: 7.2 (d, 2H), 6.4 (s, 2H), 6.3 (1H, exchanges with D₂O), 6.2 (d, 3H), 5.3 (t, 1H), 3.2 (broad doublet, 2H), 2.7 (d and s, 4H), 1.5 (d, 2H); ir (KBr): 3.25, 6.25, 6.65, 8.05, 8.6, 12.5μ].

Analysis: Calcd.: C₁₅H₁₇NO₂S.0.25H₂O: C, 64.34; H, 6.12; N, 5.00. Found: C, 64.34; H, 6.06; N, 4.95.

EXAMPLE 19

4-[2-Hydroxy-2-(4-nitrophenyl)ethylthiomethyl]pyridine

Under a nitrogen atmosphere, alpha-(4-picolylthio)-p-nitroacetophenone (0.45 g., 1.56 mmoles) and sodium cyanoborohydride (0.10 g., 1.56 mmoles) were dissolved in 15 ml. of dry methanol and a trace of bromocressol green pH indicator added (blue at 5.5, yellow at pH 3.8). The reaction was blue-green in color. Methanolic hydrogen chloride was added dropwise until the reaction turned yellow (pH approximately 4). Small additions of the methanolic hydrogen chloride were made, whenever the reaction darkened, for a period of 4 hours. The reaction was then left to stir for an additional 16 hours. The reaction mixture was concentrated to an oil which was taken up in 10 ml. of water and the product extracted into ethyl acetate (3 times 20 ml.). The combined ethyl acetate was back-washed with saturated sodium bicarbonate (2 times 15 ml.) and then with saturated sodium chloride, dried over anhydrous sodium sulfate and evaporated to yield 4-[2-hydroxy-2-(4-nitrophenyl)ethylthiomethyl]pyridine [0.347 g.; m.p. 135°–137° C.; ir (KBr): 3.25, 6.25, 6.6, 7.35, 9.35, 11.75, 13.75μ; pnmr/DMSO-d₆/TMS/τ: 7.2 (d, 2H), 6.5 (broad s, 1H). 6.2 (s, 2H), 5.1 (t, 1H), 2.6 (d, 2H), 2.3 (d, 2H), 1.7 (d, 2H), 1.4 (d, 2H)].

Analysis: Calcd.: C₁₄H₁₄N₂O₃S.0.5H₂O: C, 56.23; H, 5.05; N, 9.36. Found: C, 56.50; H, 4.87; N, 9.50.

EXAMPLE 20

4-(1-Hydroxy-1-phenyl-2-propylthiomethyl)pyridine

Under a nitrogen atmosphere, alpha-(4-picolylthio)-propiophenone (2.0 g., 7.8 mmoles) was dissolved in 20 ml. of stirring ethanol. Sodium borohydride (0.48 g., 12.4 mmoles) was added portionwise over a 10 minute period and the reaction mixture then refluxed gently for 0.5 hour, cooled and then evaporated to dryness. The residue was taken up in water, made acidic with 1 N hydrochloric acid to decompose excess borohydride, made strongly basic with 20% sodium hydroxide, and the product multiply extracted into ethyl acetate. The combined ethyl acetate extracts were back-extracted with saturated sodium chloride, dried over anhydrous magnesium sulfate, and concentrated to an oil. The oil was chromatographed on 60 g. of silica gel with 1:1 hexane:ethyl acetate as eluant. The product-containing fractions were combined and evaporated to yield 4-(1-hydroxy-1-phenyl-2-propylthiomethyl)pyridine [1.45 g.; oil; pnmr/CDCl₃/TMS/τ: 8.8 (d, 3H), 7.0 (m, 2H, 1H exchanges with D₂O), 6.4 (s, 2H), 5.5 (q, 1H), 2.7 (s, 5H), 2.7 (m, 2H), 1.5 (m, 2H); ir (CHCl₃): 3.25–3.5, 5.80, 6.25, 6.95, 8–8.25, 10.05μ].

Analysis: Calcd.: C₁₅H₁₇NOS: C, 69.48; H, 6.61; N, 5.40; m/e 259. Found: C, 69.00; H, 6.54; N, 5.14; m/e 259.

Using the methodology of Examples 16 to 20, 4-picolylthioacetaldehyde is converted to 4-(2-hydroxyethyl)pyridine, alpha-[2-(4-pyridyl)ethylthio]acetophenone is converted to 4-[2-(1-phenyl-2-hydroxyethylthio)ethyl]pyridine, and 2-(4-pyridyl)ethylthioacetone is converted to 4-[2-(2-hydroxy-1-propylthio)ethyl]pyridine.

EXAMPLE 21

4-(2-Hydroxy-2-methyl-1-propylthiomethyl)pyridine

Under a nitrogen atmosphere, 4-picolylthioacetone (2.0 g., 11 mmoles) was dissolved in 45 ml. of dry tetrahydrofuran and cooled to 0° C. A solution of methylmagnesium bromide in diethylether (3M, 4 ml., 12 mmoles) was added slowly. After addition was complete, the reaction mixture was allowed to warm to room temperature and left to stir for approximately 64 hours. Saturated ammonium chloride (approximately 50 ml.) was added to the reaction mixture, which was then extracted with ethyl acetate (4 times 50 ml.). The combined extracts were extracted with saturated sodium chloride, dried over anhydrous magnesium sulfate and evaporated to an oil (1.5 g.). The oil was chromatographed on 90 g. of silica gel with 19:1 chloroform:methanol as eluant. After a forerun of approximately 300 ml., 15 ml. fractions were taken. Fractions 18–25 were combined and concentrated to yield 4-(2-hydroxy-2-methyl-1-propylthiomethyl)pyridine [0.51 g.; oil; ir (film): 3.0, 3.35, 6.25, 7.05, 8.25, 8.70, 11.0, 12.25μ; pnmr/CDCl₃/TMS/τ: 8.6 (s, 6H), 7.3 (s, 2H), 7.1 (s, 1H), 6.1 (s, 2H), 2.6 (d, 2H), 1.4 (d, 2H)].

Analysis: Calcd.: C₁₀H₁₅NOS: C, 60.9; H, 7.7; N, 7.1; m/e 197. Found: C, 60.5; H, 7.5; N, 7.5; m/e 197.

By use of the same methodology, alpha-(4-picolylthio)acetophenone is converted to 4-(2-hydroxy-2-phenyl-1-propylthiomethyl)pyridine, 4-picolylthioacetaldehyde is converted to 4-(2-hydroxy-1-propylthiomethyl)pyridine, and alpha-[2-(4-pyridyl)ethylthio]acetophenone is converted to 4-[2-(2-hydroxy-2-phenyl-1-propylthio)ethyl]pyridine.

By use of the same methodology, except to use 2.1 equivalents of methylmagnesium bromide, ethyl 4-picolylthioacetate is converted to 4-(2-hydroxy-2-methyl-1-propylthiomethyl)pyridine and methyl 2-[2-(4-pyridyl)ethylthio]acetate is converted to 4-[2-(2-hydroxy-2-methyl-1-propylthio)ethyl]pyridine.

By use of the same methodology, but using an equivalent amount of phenylmagnesium bromide for methyl magnesium bromide, 4-picolylthioacetone is converted to 4-(2-hydroxy-2-phenyl-1-propylthiomethyl)pyridine and 2-(4-pyridyl)ethylthioacetone is converted to 4-[2-(2-hydroxy-2-phenyl-1-propylthio)ethyl]pyridine.

EXAMPLE 22

Methyl 3-(4-picolylthio)propionate

Under a nitrogen atmosphere, sodium methoxide (3.7 g., 68 mmoles) was dissolved in 45 ml. of methanol and cooled in an ice bath. 4-Picolyl chloride hydrochloride (5.0 g., 30 mmoles) suspended in 7.5 ml. of methanol was added slowly. After 10 minutes, a solution of methyl 3-mercaptopropionate in 7.5 ml. of methanol was added over 10 minutes. The reaction mixture was warmed to room temperature and stirred for approximately 16 hours. The reaction mixture was filtered and the mother liquor concentrated to an oil. The oil was chromatographed on 250 g. of silica gel, employing a short length, wide width column, with ethyl acetate as eluant. Product-containing fractions were combined and evaporated to yield methyl 3-(4-picolylthio)acetate [63 g.; oil; pnmr/CDCl$_3$/TMS/$\tau$: 7.4 (s, d, 4H), 6.3 (s, 5H), 2.7 (d, 2H), 1.6 (d, 2H); ir (film): 3.0, 3.5, 5.80, 6.25, 7.0, 7.15, 12.25$\mu$].

Analysis: Calcd. for: C$_{10}$H$_{13}$NO$_2$S.0.25H$_2$O: C, 55.74; H, 6.27; N, 6.49; m/e 211. Found: C, 55.87; H, 5.99; N, 6.59; m/e 211.

EXAMPLE 23

4-(3-Hydroxypropylthiomethyl)pyridine

Under a nitrogen atmosphere, stirred Red-al solution (2.04 ml., 10.4 mmoles) was coold to 0° C. A solution of methyl 3-(4-picolylthio)propionate in 10 ml. of dry tetrahydrofuran was added slowly. The reaction mixture was warmed to room temperature and stirred for 45 minutes. The reaction mixture was slowly added to 25 ml. of cold, 1 N HCl, solids removed by filtration and the mother liquor extracted with four 25 ml. portions of ethyl acetate. The combined extracts were dried over anhydrous sodium sulfate, filtered and concentrated to yield 4-(3-hydroxypropylthio)pyridine [1.40 g.; oil; pnmr/CDCl$_3$/TMS/$\tau$: 8.1 (q, 2H), 7.4 (t, 2H), 6.4 (t, 2H), 6.3 (d, 2H), 1.5 (d, 2H); ir (film): 3.1, 3.5, 6.25, 7.1, 9.5, 12.25$\mu$].

Analysis: Calcd. for C$_9$H$_{13}$NO$_5$: C, 58.98; H, 7.15; N, 7.64. Found: C, 58.77; H, 7.11; N, 7.67.

EXAMPLE 24

4-(2-Acetoxyethylthiomethyl)pyridine 4-(2-Hydroxyethylthiomethyl)pyridine (1.0 g.) was refluxed with 10 ml. of acetic anhydride for 3 hours. After standing overnight at room temperature, the acetic anhydride was evaporated in vacuo, the residue diluted with 10 ml. of water, made basic with sodium bicarbonate, and the product extracted into chloroform (four times 50 ml.). The chloroform was carbon treted, dried and concentrated to an oil (1.47 g.). The oil was chromatographed on 60 g. of silica gel with 5% methanol/chloroform as eluant. Fractions containing only product (Rf 0.6 on thin layer silica gel chromatography eluted with 18:1 chloroform:methanol) were combined and concentrated to yield 4-(2-acetoxyethylthiomethyl)pyridine [300 mg. of oil; pnmr/CDCl$_3$/TMS/$\tau$: 7.9 (s, 3H), 7.3 (t, 2H), 6.3 (s, 2H), 5.8 (t, 2H), 2.7 (d, 2H), 1.4 (d, 2H)].

By the same methodology, the following acetyl derivatives can be prepared from the corresponding alcohols:
4-(2-acetoxy-1-propylthiomethyl)pyridine,
4-(3-acetoxy-2-butylthiomethyl)pyridine,
4-(2-acetoxyphenylthiomethyl)pyridine,
4-(1-acetoxy-2-propylthiomethyl)pyridine,
4-(1-phenyl-2-acetoxyethylthiomethyl)pyridine,
4-(2-acetoxy-1-propylthiomethyl)pyridine,
4-(2-acetoxy-2-phenylethylthiomethyl)pyridine,
4-[2-(4-methoxyphenyl)-2-acetoxyethylthiomethyl]pyridine,
4-[2-acetoxy-2-(4-nitrophenyl)ethylthiomethyl]pyridine,
4-(1-acetoxy-1-phenyl-2-propylthiomethyl)pyridine,
4-(2-acetoxy-2-methyl-1-propylthiomethyl)pyridine,
4-[2-(2-acetoxyethylthio)ethyl]pyridine,
4-[2-(2-acetoxyphenylthio)ethyl]pyridine and
4-(3-acetoxypropylthio)pyridine.

By the same methodology, substituting an equivalent amount of the appropriate acid anhydride and a reaction temperature of 100°–130° C., the corresponding propionic, isopropionic, butyric, isobutyric, valeric, and isovaleric acid esters can also be prepared.

4-(2-Hydroxyethylthiomethyl)pyridine can also be reacted with one equivalent of acetyl chloride, propionyl chloride, isopropionyl chloride, butyryl chloride, isobutyryl chloride or benzoyl chloride in refluxing chloroform to form the corresponding esters. The products can be isolated as hydrochloride salts by removal of solvent when reaction is complete. The hydrochloride salts can be converted to the free base form by treatment with a small excess of aqueous sodium hydroxide, extraction into chloroform, and solvent removal.

EXAMPLE 25

4-(2-Methoxyethylthiomethyl)pyridine

Sodium hydride (170 mg., 7.1 mmoles, from 340 mg. of 50% dispersion in oil washed, under nitrogen, with hexane) was slurried in 5 ml. of dry tetrahydrofuran. A solution of 4-(2-hydroxyethylthiomethyl)pyridine (1.0 g., 5.9 mmoles) in 10 ml. ws added dropwise over 5 minutes and the mixture stirred for 5 minutes. Finally, methyl iodide (260 mg., 0.1 ml., 5.9 mmoles) in 2 ml. of tetrahydrofuran was added and the mixture stirred overnight. The reaction mixture was clarified by filtration and evaporated to an oil (approximately 1.3 g.) which was chromatographed on silica gel with chloroform as eluent. Pure fractions of product were combined and concentrated to yield 4-(2-methoxyethylthiomethyl)pyridine [210 mg. of oil; m/e 183; pnmr/CDCl$_3$/TMS/$\tau$: 7.4 (t, 2H), 6.7 (s, 3H), 6.5 (t, 2H), 6.3 (s, 2H), 2.7 (d, 2H), 1.4 (d, 2H)].

By the same methodology, the following methyl ethers can be prepared from the corresponding alcohols:
4-(2-methoxy-1-propylthiomethyl)pyridine,
4-(3-acetoxy-2-butylthiomethyl)pyridine,
4-(2-methoxyphenylthiomethyl)pyridine,
4-(1-methoxy-2-propylthiomethyl)pyridine,
4-(1-phenyl-2-metoxyethylthiomethyl)pyridine,
4-(2-methoxy-1-propylthiomethyl)pyridine,
4-(2-methoxy-2-phenylethylthiomethyl)pyridine, 4-[2-(4-methoxyphenyl)-2-methoxyethylthiomethyl]-pyridine,
4-[2-methoxy-2-(4-nitrophenyl)ethylthiomethyl]pyridine,
4-(1-methoxy-1-phenyl-2-propylthiomethyl)pyridine,
4-(2-methoxy-2-methyl-1-propylthiomethyl)pyridine,
4-[2-(2-methoxyethylthio)ethyl]pyridine,
4-[2-(2-methoxyphenylthio)ethyl]pyridine and
4-(3-methoxypropylthio)phyridine.

EXAMPLE 26

4-[2-(2-Hydroxyethylthio)ethyl]pyridine

Under a nitrogen atmosphere, sodium methoxide (1.62 g., 0.03 mole) was dissolved in 36 ml. of stirring absolute ethanol and the solution cooled in an ice bath. 2-Mercaptoethanol (2.34 g., 0.03 mole) in 6 ml. of absolute ethanol was added over approximately 5 minutes. Finally, 4-vinylpyridine (3.22 g., 0.03 mole) in approximately 20 ml. of absolute ethanol was added over 15 minutes. The reaction mixture was allowed to warm to room temperature and stirred for 23 hours. The reaction mixture was concentrated to a thick oil (7.28 g.). The oil was diluted with a small amount of chloroform (a strong exotherm occurred, leading to refluxing of the chloroform) and chromatographed on silica gel, with large volumes of chloroform and finally chloroform/1% methanol as eluant. Product containing fractions (from the latter eluant) were combined and evaporated to yield the free base of 4-[2-(2-hydroxyethylthio)ethyl]pyridine [2.49 g.; oil; m/e calcd.: 183, found: 183; ir (film): 3.10, 3.45, 3.52, 6.23, 7.07, 9.40, 9.57, 9.98 and 12.44$\mu$; pnmr/CDCl$_3$/TMS/$\delta$: 8.53 (m, 2H), 7.17 (m, 2H), 3.77 (t, 2H), 3.57 (s, 1H, exchanges with D$_2$O), 2.85 (m, 4H) and 2.73 ppm (t, 2H)].

The method is improved by adding the initially obtained oil slowly to a stirred mixture of water and chloroform. The chloroform phase is separated and the aqueous phase further extracted with chloroform. The combined chloroform phases are extracted with saturated sodium chloride, dried over anhydrous sodium sulfate, and stripped to a volume suitable for placement on the silica gel column which is eluted directly with chloroform/1% methanol.

By the same method 4-viylpyridine is reacted with 2-mercaptophenol to yield 4-[2-(2-hydroxyphenylthio)ethylpyridine, with mercaptoacetone to yield 2-(4-pyridyl)ethylthioacetone, and with methyl 2-mercaptoacetate (preferably in methanol rather than ethanol solution) to yield methyl 2-[2-(4-pyridyl)ethylthio]acetate.

EXAMPLE 27

4-(2-Hydroxyethylthiomethyl)pyrimidine

Under a nitrogen atmosphere, sodium methoxide (1.19 g., 22 mmoles) was dissolved in 23.2 ml. of absolute ethanol, and the stirred solution cooled in an ice bath. 2-Mercaptoethanol (1.56 g., 20 mmoles) in 4 ml. of absolute ethanol was added over approximately 5 minutes. Crude 4-pyrimidylmethyl bromide (3.74 g., prepared according to Preparation 5) dissolved in 10 ml. of ethanol was then added over approximately 15 minutes. The reaction mixture was allowed to warm and stirred for 16 hours at room temperature. Solids were removed by filtration with diatomaceous earth. The filter cake was repulped with ethanol and the filtrate combined with the original filtrate and stripped of solvent. The resulting semi-solid was taken up in approximately 35 ml. of refluxing chloroform, solids removed by filtration, and the filtrate concentrated to an oil (1.64 g.). The oil was redissolved in chloroform and chromatographed on 71 g. of silica gel with fractions of 25 ml. volume collected. The eluant was initially chloroform, then chloroform/0.5% methanol (fractions 181–220), and finally chloroform/1% methanol (fractions 221–320). Fractions 161–229 were combined, as were fractions 230–320, and evaporated separately to yield two batches of relatively pure product (0.42 g. and 1.09 g., respectively). The larger batch, which contained some solids, was taken up in approximately 20 ml. of chloroform, clarified by filtration, and reconcentrated to yield purified 4-(2-hydroxyethylthiomethyl)pyrimidine [0.62 g.; oil; ir (film): 3.00, 3.43, 3.47, 6.29, 7.19, and 9.41$\mu$; pnmr/CDCl$_3$/TMS/$\delta$: 9.20 (s, 1H), 8.75 (d, 1H), 7.43 (d, 1H), 4.17-3.33 (m, 5H, 1H exchanges with D$_2$O) and 2.47 ppm (q, 2H)].

By the same method, 4-pyrimidylmethyl bromide is reacted with 3-mercapto-2-butanol to yield 4-(3-hydroxy-2-butylthiomethyl)pyrimidine, with 3-mercapto-1,2-propanediol to yield 4-(2,3-dihydroxy-1-propylthiomethyl)pyrimidine, with 2-mercaptophenol to yield 4-(2-hydroxyphenylthiomethyl)pyrimidine, with ethyl 2-mercaptoacetate to yield ethyl 2-(4-pyrimidylmethylthio)acetate, with ethyl 2-mercaptopropionate to yield ethyl 2-(4-pyrimidylmethylthio)propionate, with ethyl 2-phenyl-2-mercaptoacetate to yield ethyl 2-phenyl-2-(4-pyrimidylmethylthio)acetate (when ethyl esters are prepared, it is preferable to substitute an equivalent of sodium ethoxide for sodium methoxide), with mercaptoacetone to yield 4-pyrimidylmethylthioacetone, with 1-phenyl-1-mercaptoacetone to yield 1-(4-pyrimidylmethylthio)-1-phenylacetone, and with methyl 3-mercaptopropionate to yield methyl 3-(4-pyrimidylmethylthio)propionate (when methyl esters are prepared it is preferable to substitute methanol for ethanol).

EXAMPLE 28

2-(4-Pyrimidyl)ethylthio Derivatives

Employing the methodology of Examples 1 to 4, 2-(4-pyrimidyl)ethyl chloride hydrochloride is reacted with 2-mercaptoethanol to yield 4-[2-(2-hydroxyethylthio)ethyl]pyridine, with 3-mercapto-2-butanol to yield 4-[2-(3-hydroxy-2-butylthio)ethyl]pyrimidine, with 3-mercapto-1,2-propanediol to yield 4-[2-(2,3-dihydroxy-1-propylthio)ethyl]pyrimidine, with 2-mercaptophenol to yield 4-[2-(2-hydroxyphenylthio)ethyl]pyrimidine, with ethyl 2-mercaptoacetate to yield ethyl 2-[2-(4-pyrimidyl)ethylthio]acetate, with ethyl 2-mercaptopropionate to yield ethyl 2-[2-(4-pyrimidyl)ethylthio]propionate, with ethyl 2-phenyl-2-mercaptoacetate to yield ethyl 2-phenyl-2-[2-(4-pyrimidyl)ethylthio]acetate (when ethyl esters are prepared, it is preferable to substitute an equivalent amount of sodium ethoxide for sodium methoxide), with mercaptoacetone to yield 1-[2-(4-pyrimidyl)ethylthio]acetone and with 1-phenyl-1-mercaptoacetone to yield 1-[2-(4-pyrimidyl)ethylthio]-1-phenylacetone.

EXAMPLE 29

4-Pyrimidylmethylthio Derivatives

According to the methodology of Examples 11 to 15, 4-pyrimidylmethyl mercaptan is reacted with 2-chloroethanol or 2-bromoethanol to yield 4-(2-hydroxyethylthiomethyl)pyrimidine, with chloroacetone to yield 4-pyrimidylmethylthioacetone, with alpha-bromoacetophenone to yield alpha-(4-pyrimidylmethylthio)acetophenone, with alpha-bromo-p-methoxyacetophenone to yield alpha-(4-pyrimidylmethylthio)-p-methoxyacetophenone, with alpha-bromo-p-nitroacetophenone to yield alpha-(4-pyrimidylmethylthio)-p-nitroacetophenone, with alpha-bromopropiophenone to yield alpha-(4-pyrimidylmethylthio)propiophenone, with ethyl 2-bromoacetate to yield 2-(4-pyrimidylmethylthio)acetate, with ethyl 2-chloropropionate to yield 2-(4-pyrimidylmethylthio)propionate and with ethyl 2-phenyl-2-bromoacetate to yield 2-phenyl-2-(4-pyrimidylmethylthio)acetate (when ethyl esters are prepared, it is preferable to substitute an equivalent of sodium ethoxide for sodium methoxide; when the corresponding methyl esters are prepared, it is preferable to substitute methanol for ethanol).

EXAMPLE 30

Reduction of Pyrimidine-Esters

According to the Red-al reduction procedure of Examples 9 and 10, ethyl or methyl 2-(4-pyrimidylmethylthio)acetate is converted to 4-(2-hydroxyethylthiomethyl)pyrimidine, ethyl or methyl 2-(4-pyrimidylmethylthio)propionate is converted to 4-(1-hydroxy-2-propylthiomethyl)pyrimidine, ethyl or methyl 2-phenyl-2-(4-pyrimidylmethylthio)acetate is converted to 4-(1-phenyl-2-hydroxyethylthiomethyl)pyrimidine, ethyl 2-[2-(4-pyrimidyl)ethylthio]acetate is converted to 4-[2-(2-hydroxyethylthio)ethyl]pyrimidine, 2-[2-(4-pyrimidyl)ethylthio]propionate is converted to 4-[2-(1-hydroxy-2-propylthio)ethyl]pyrimidine, ethyl 2-phenyl-2-[2-(4-pyrimidyl)ethyl]thioacetate is converted to 4-[2-(1-phenyl-2-hydroxyethylthio)ethyl]pyrimidine, and methyl 3-(4-pyrimidylmethylthio)propionate is converted to 4-(3-hydroxypropylthiomethyl)pyrimidine.

The same method is also used to reduce the ketones of Examples 27 to 29 to the corresponding alcohols.

EXAMPLE 31

Reduction of Pyrimidine-Ketones

According to the sodium borohydride/sodium cyanoborohydride reduction procedures of Examples 16–20, 4-pyrimidylmethylthioacetone is converted to 4-(2-hydroxy-1-propylthiomethyl)pyrimidine, 1-(4-pyrimidylmethylthio)-1-phenylacetone is converted to 4-(1-phenyl-2-hydroxy-1-propylthiomethyl)pyrimidine, alpha-(4-pyrimidylmethylthio)acetophenone is converted to 4-(2-hydroxy-2-phenylethylthiomethyl)pyrimidine, alpha-(4-pyrimidylmethylthio)-p-methoxyacetophenone is converted to 4-[2-hydroxy-2-(4-methoxyphenyl)ethylthiomethyl]pyrimidine, alpha-(4-pyrimidylmethylthio)-p-nitroacetophenone is converted to 4-[2-hydroxy-2-(4-nitrophenyl)ethylthiomethyl]pyrimidine, alpha-(4-pyrimidylmethylthio)propiophenone is converted to 4-(1-hydroxy-1-phenyl-2-propylthiomethyl)pyrimidine, 1-[2-(4-pyrimidyl)ethylthio]acetone is converted to 4-[2-(2-hydroxy-1-propylthio)ethyl]pyrimidine, and 1-[2-(4-pyrimidyl)ethylthio]-1-phenylacetone is converted to 4-[2-(2-hydroxy-1-phenyl-1-propylthio)ethyl]pyrimidine.

EXAMPLE 32

Action of Grignard Reagents on Pyrimidine Ketones and Pyrimidine Esters

According to the methodology of Example 21, one equivalent of methylmagnesium bromide is reacted with 4-pyrimidylmethylthioacetone to yield 4-(2-hydroxy-2-methyl-1-propylthiomethyl)pyrimidine, with 1-(4-pyrimidylmethylthio)-1-phenylacetone to yield 4-(1-phenyl-2-hydroxy-2-methyl-1-propylthiomethyl)pyrimidine, with alpha-(4-pyrimidylmethylthio)acetophenone to yield 4-(2-hydroxy-2-phenyl-1-propylthiomethyl)pyrimidine, with alpha-(4-pyrimidylmethylthio)propiophenone to yield 4-(3-hydroxy-3-phenyl-2-butylthiomethyl)pyrimidine, with 1-[2-(4-pyrimidyl)ethylthio]acetone to yield 4-[2-(2-hydroxy-2-methyl-1-propylthio)ethyl]pyrimidine and with 1-[2-(4-pyrimidyl)ethylthio]-1-phenylacetone to yield 4-[2-(1-phenyl-2-hydroxy-2-methyl-1-propylthio)ethyl]pyrimidine.

EXAMPLE 33

Pyrimidine Esters

According to the methods of Example 24, by the action of the appropriate acid chloride, acid anhydride or mixed anhydride, the alcohols prepared by Examples 27 32 are converted to the corresponding esters. In such manner, the following compounds are prepared:
4-(2-acetoxyethylthiomethyl)pyrimidine,
4-(2-propionyloxyethylthiomethyl)pyrimidine,
4-(2-butyryloxyethylthiomethyl)pyrimidine,
4-(2-isobutyryloxyethylthiomethyl)pyrimidine,
4-(2-valeryloxyethylthiomethyl)pyrimidine,
4-(2-isovaleryloxyethylthiomethyl)pyrimidine,
4-(2-benzoyloxyethylthiomethyl)pyrimidine,
4-(2-acetoxy-1-propylthiomethyl)pyrimidine,
4-(1-acetoxy-2-propylthiomethyl)pyrimidine,
4-(3-acetoxy-2-butylthiomethyl)pyrimidine,
4-(2-acetoxy-1-phenylethylthiomethylpyrimidine and
4-[2-(2-acetoxyethylthio)ethyl]pyrimidine.

EXAMPLE 34

Pyrimidine Ethers

According to the method of Example 25, by the action of methyl iodide, the alcohols prepared by Examples 27 to 32 are converted to the corresponding methyl esters. In such manner, the following are prepared:
4-(2-methoxyethylthiomethyl)pyrimidine,
4-(2-methoxy-1-propylthiomethyl)pyrimidine,
4-(1-methoxy-2-propylthiomethyl)pyrimidine,
4-(3-methoxy-2-butylthiomethyl)pyrimidine,
4-(2-methoxy-2-phenylethylthiomethyl)pyrimidine and
4-[2-(2-methoxyethylthio)ethyl]pyrimidine.

EXAMPLE 35

Pyrimidine Salts

Acid addition salts of the pyrimidine alcohols, esters and ethers of Examples 27 to 34 are prepared by dissolving the pyrimidine in ethanol. An equimolar amount of the desired acid is dissolved in a separate quantity of ethanol. The two solutions are combined and the salt precipitated by the addition of ether, or obtained by stripping of solvent. In this manner, the following salts are prepared:
4-(2-hydroxyethylthiomethyl)pyrimidinium dihydrogenphosphate,
4-(2-hydroxyethylthiomethyl)pyrimidine hydrochloride,
4-(2-hydroxyethylthiomethyl)pyrimidinium p-toluenesulfonate,
4-(2-hydroxyethylthiomethyl)pyrimidinium methanesulfonate,
4-(2-hydroxyethylthiomethyl)pyrimidinium bisulfate, 4-(2-acetoxyethylthiomethyl)pyrimidine hydrochloride,
4-(2-methoxyethylthiomethyl)pyrimidinium bisulfate,
4-(3-hydroxy-2-butylthiomethyl)pyrimidinium p-toluenesulfonate,
4-[2-(2-hydroxyethylthio)ethyl]pyrimidine hydrochloride,
4-(2,3-dihydroxy-1-propylthiomethyl)pyrimidinium dihydrogenphosphate.

EXAMPLE 36

Capsules

A dry solid pharmaceutical composition is prepared by blending the following materials together in the proportions by weight indicated below:

| | |
|---|---|
| 4-(2-Hydroxyethylthiomethyl)pyridinium dihydrogenphosphate | 12 |
| Calcium carbonate | 20 |
| Polyethylene glycol, average molecular weight, 4000 | 72 |

The dried solid mixture so prepared is then thoroughly agitated so as to obtain a uniform powder. Soft elastic gelatin capsules containing this pharmaceutical composition are then prepared in potencies (equivalent to weight of free base) of 12.5 mg., 25 mg. and 50 mg. by filling with an appropriate amount of the uniform powder.

For higher potency capsules, e.g. 100 mg. capsules, a lower proportion of the inert ingredients is employed in preparation of the uniform powder for encapsulation.

To make hard gelatin filled capsules, the amount of inert ingredients is adjusted so as to conveniently fill standard sized gelatin capsules with the desired drug potency.

Alternative blends for encapsulation are prepared from lactose and cornstarch in a proportion 33 to 1 to 10 to 1, with small portion of talc if desired, combined with active ingredient sufficient to provide potencies as above when filled into capsules.

EXAMPLE 37

A dry solid pharmaceutical composition is prepared by blending the following materials together in the proportions by weight specified below:

| | |
|---|---|
| 4-(2-Hydroxyethylthiomethyl)pyridinium dihydrogenphosphate | 30 |
| Sodium citrate | 37.5 |
| Alginic acid | 15 |
| Polyvinylpyrrolidone | 15 |
| Magnesium stearate | 7.5 |

After thorough blending, tablets are punched from the resulting mixture, said tablets containing 25 mg. or 50 mg. (as weight equivalent to the free base) of the active ingredient. In a like manner, with variation in the proportion of inert ingredients if desired, tablets of 5 mg., 10 mg., 75 mg. and 100 mg. potency are also prepared.

An alternative tablet base is prepared by blending the following ingredients:

| | |
|---|---|
| 4-(2-Hydroxyethylthiomethyl)pyridinium dihydrogenphosphate | 30 |
| Sucrose, U.S.P. | 55 |
| Tapioca starch | 15 |
| Magnesium stearate | 6.5 |

Tablets of the desired potency are then punched from this blend.

PREPARATION 1

4-Picolylisothiouronium chloride hydrochloride

Thiourea (11.42 g., 0.15 moles) was suspended with stirring in 45 ml. of absolute ethanol. The suspension was heated to reflux under nitrogen and a suspension of finely divided 4-picolyl chloride hydrochloride (25.37 g., 0.15 moles) in approximately 100 ml. of absolute ethanol was added over 15 minutes, with external heating removed as necessary to avoid overly vigorous reflux. After 6 hours additional reflux, the reaction mixture was cooled to room temperature and filtered, with cold ethanol wash, to yield 4-picolylisothiouronium chloride hydrochloride (35.8 g.; m.p. 226°-227° C. (dec.); ir (KBr): 3.40, 6.05, 6.14, 6.27, 6.71 and 12.34μ).

Analysis: Calcd. for $C_7H_9N_3S \cdot 2HCl$: C, 35.01; H, 4.62; N, 17.50. Found: C, 35.04, H, 4.61; N, 17.55.

The same method is used to convert 2-(4-pyridyl)ethyl chloride to 2-(4-pyridyl)ethylisothiouronium chloride.

PREPARATION 2

4-Picolyl Mercaptan

4-Picolylisothiouronium chloride hydrochloride (32.4 g., 0.135 moles) was dissolved in 45 ml. of water with stirring, a warm solution of sodium hydroxide (11.02 g., 0.27 mole) in 18 ml. of water was added dropwise over approximately 10 minutes during which oil droplets began to form. The mildly exothermic reaction was allowed to stir for approximately 30 minutes, at which time the pH was increased from 7 to 8 by the addition of sodium. The pH was then reduced to 6 by the slow addition of 6 N hydrochloric acid. The oily product was extracted into ether (three 125 ml. portions). The combined ether extracts were dried over anhydrous sodium sulfate, and evaporated to an oil containing solids, with a potent mercaptan odor (11.18 g.). Fractional distillation gave purified 4-picolyl mercaptan (4.47 g.; b.p. 109°-104° C./15 mm.; thin layer chromatography on silica gel: Rf 0.65-0.7 when eluted with 4CHCl₃/1CH₃OH). This mercaptan readily forms a solid disulfide when contacted with air.

The same method is used to convert 2-(4-pyridyl)ethylisothiouronium chloride to 2-(4-pyridyl)ethyl mercaptan.

PREPARATION 3

4-Picolyl Acetate

4-Picoline N-oxide (250 g.) was dissolved in a mixture of 2.5 l. of acetic acid and 425 ml. of acetic anhydride. The solution was slowly heated to reflux and refluxed for about 22 hours. The reaction mixture was then stripped of acetic acid and acetic anhydride and the residual oil vacuum distilled, using a 6 inch fractionation column. Material boiling at a pot temperature of 100° C. and a head temperature of 82° C. at 1.2 mm. was combined, yielding 305.9 g. of an 87:13 mixture of 4-picolyl acetate and 3-acetoxy-4-picoline.

PREPARATION 4

4-Picolyl Bromide Hydrobromide

4-Picolylacetate (300 g., 87% pure) was combined with 3.0 l. of 48% hydrobromic acid. A spontaneous exotherm occurred, the temperature rising from 26° to 42° C. The mixture was heated to reflux and refluxed for about 1 hour (pot temperature 124° C.). The reaction mixture was then concentrated in vacuo to yield a gummy solid which was dissolved in 1500 ml. of absolute alcohol. Crude hydrobromide salt (379 g.) crystallized on chilling and was recovered by filtration. Purified 4-picolylbromide hydrobromide (33.1 g., m.p. 187.5°–189° C.) was obtained by recrystallization of 50 g. of crude from absolute alcohol.

PREPARATION 5

4-Pyrimidylmethyl Bromide

Under a nitrogen atmosphere, finely divided N-bromosuccinimide (4.45 g., 25 mmoles) was suspended in 75 ml. of dry carbon tetrachloride (distilled from $P_2O_5$). The stirred suspension was added 4-methylpyrimidine (97% pure, 1.94 g., 20 mmoles). Benzoyl peroxide (0.44 g., 1.8 mmoles) was then added cautiously. The stirred reaction was heated to reflux and irradiated with a 300 watt flood light for 6 hours. The reaction mixture was then cooled in an ice bath and crude 4-pyridylmethyl bromide (3.74 g.) recovered by filtration and used directly in the next step.

4-Pyrimidylmethyl bromide is further purified by dissolution in dilute hydrobromic acid, extraction of the aqueous phase with methylene chloride, basification of the aqueous phase with sodium hydroxide and extraction of the product into methylene chloride. The methylene chloride solution is dried and evaporated to recover purified product.

PREPARATION 6

2-(4-Pyrimidyl)ethyl Chloride Hydrochloride

4-Pyrimidylmethyl bromide is converted to the nitrile, then to ethyl 4-pyrimidylacetate, then to 2-(4-pyrimidyl)ethanol and finally to 2-(4-pyrimidyl)ethyl chloride hydrochloride according to the methods detailed in Example 4.

PREPARATION 7

4-Pyrimidylmethyl Mercaptan

The methods of Preparations 1 and 2 are employed to convert 4-pyrimidylmethyl bromide to 4-pyrimidyl mercaptan via 4-pyrimidylmethylisothiouronium bromide. Half as much base is employed in the first stage of the synthesis as compared to Preparation 1, since the free base of the starting material is employed for this preparation.

We claim:

1. A compound of the formula

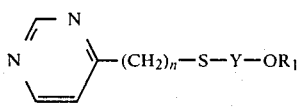

and pharmaceutically acceptable salts thereof, wherein
n is an integer of value 1 or 2;
Y is o-phenylene, propylene, ethylene (unsubstituted or substituted with up to 2 methyl groups and up to 1 phenyl group),

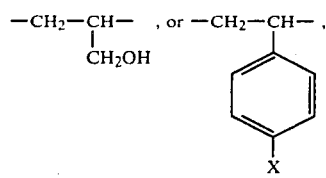

wherein X is nitro or methoxy;
$R_1$ is hydrogen, methyl, $(C_2-C_5)$alkanoyl or benzoyl;
with the proviso that when Y is

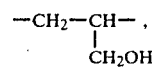

$R_1$ is hydrogen.

2. A compound of claim 1 wherein n is 1 and Y is o-phenylene, ethylene (unsubstituted or substituted with up to 2 methyl groups), or

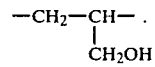

3. A compound of claim 2 wherein $R_1$ is hydrogen or acetyl.

4. A compound of claim 3 wherein Y is ethylene.

5. A compound of claim 4 wherein $R_1$ is hydrogen.

6. A pharmaceutical composition for the treatment of rheumatoid arthritis in a mammal which comprises an anti-rheumatoid arthritis compound of the formula

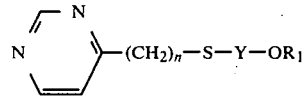

or a pharmaceutically acceptable salt thereof, wherein
n is an integer of value 1 or 2;
Y is o-phenylene, propylene, ethylene (unsubstituted or substituted with up to 2 methyl groups and up to 1 phenyl group),

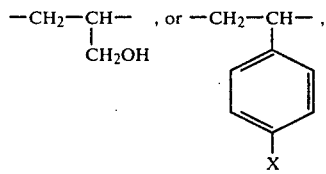

wherein X is nitro or methoxy;
$R_1$ is hydrogen, methyl $(C_2-C_5)$alkanoyl or benzoyl;
with the proviso that when Y is

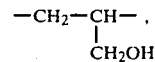

$R_1$ is hydrogen;
together with a pharmaceutically acceptable carrier.

7. The composition of claim 6 wherein n is 1 and Y is o-phenylene, ethylene (unsubstituted or substituted with up to 2 methyl groups), or

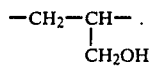

8. The composition of claim 7 wherein $R_1$ is hydrogen or acetyl.
9. The composition of claim 8 wherein Y is ethylene.
10. The composition of claim 9 wherein $R_1$ is hydrogen.
11. A method of treating rheumatoid arthritis in a mammal which comprises administering to said mammal an anti-rheumatoid arthritis amount of a compound of the formula

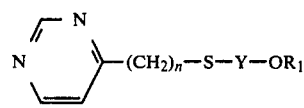

or a pharmaceutically acceptable salt thereof, wherein
n is an integer of value 1 or 2;
Y is o-phenylene, propylene, ethylene (unsubstituted or substituted with up to 2 methyl groups and up to 1 phenyl groups),

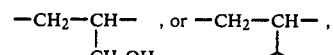

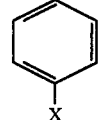

wherein X is nitro or methoxy;
$R_1$ is hydrogen, methyl, ($C_2$–$C_5$)alkanoyl or benzoyl; with the proviso that when Y is

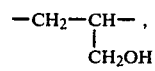

$R_1$ is hydrogen.

12. The method of claim 11 wherein n is 1 and Y is o-phenylene, ethylene (unsubstituted or substituted with up to 2 methyl groups), or

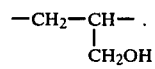

13. The method of claim 12 wherein $R_1$ is hydrogen or acetyl.
14. The method of claim 13 wherein Y is ethylene.
15. The method of claim 14 wherein $R_1$ is hydrogen.

* * * * *